US012636311B2

(12) United States Patent
Hahn

(10) Patent No.: US 12,636,311 B2
(45) Date of Patent: *May 26, 2026

(54) TOPICALLY ADMINISTERED STRONTIUM-CONTAINING COMPLEXES FOR TREATING PAIN, PRURITIS AND INFLAMMATION

(71) Applicant: Galleon Labs LLC, Naples, FL (US)

(72) Inventor: Gary S. Hahn, San Diego, CA (US)

(73) Assignee: GALLEON LABS LLC, Naples, FL (US)

( * ) Notice: Subject to any disclaimer, the term of this patent is extended or adjusted under 35 U.S.C. 154(b) by 290 days.

This patent is subject to a terminal disclaimer.

(21) Appl. No.: 18/487,938

(22) Filed: Oct. 16, 2023

(65) Prior Publication Data

US 2024/0041919 A1    Feb. 8, 2024

Related U.S. Application Data

(60) Division of application No. 17/100,652, filed on Nov. 20, 2020, now Pat. No. 11,801,261, which is a continuation of application No. 16/189,578, filed on Nov. 13, 2018, now Pat. No. 10,874,689, which is a continuation of application No. 15/284,892, filed on Oct. 4, 2016, now Pat. No. 10,159,693, which is a continuation of application No. 14/493,202, filed on Sep. 22, 2014, now Pat. No. 9,480,704, which is a division of application No. 14/386,731, filed as application No. PCT/US2013/032608 on Mar. 15, 2013, now Pat. No. 9,333,185.

(60) Provisional application No. 61/613,923, filed on Mar. 21, 2012.

(51) Int. Cl.
| | |
|---|---|
| *A61K 33/00* | (2006.01) |
| *A61K 9/00* | (2006.01) |
| *A61K 31/192* | (2006.01) |
| *A61K 31/198* | (2006.01) |
| *A61K 31/265* | (2006.01) |
| *A61K 33/24* | (2019.01) |
| *A61P 17/00* | (2006.01) |
| *A61P 17/18* | (2006.01) |
| *A61P 29/00* | (2006.01) |

(52) U.S. Cl.
CPC ............ *A61K 33/00* (2013.01); *A61K 9/0014* (2013.01); *A61K 31/192* (2013.01); *A61K 31/198* (2013.01); *A61K 31/265* (2013.01); *A61K 33/24* (2013.01); *A61P 17/00* (2018.01); *A61P 17/18* (2018.01); *A61P 29/00* (2018.01)

(58) Field of Classification Search
CPC .................. A61P 17/00; A61K 33/00
See application file for complete search history.

(56) References Cited

U.S. PATENT DOCUMENTS

| | | | |
|---|---|---|---|
| 3,833,732 | A | 9/1974 | Saeed et al. |
| 4,477,439 | A | 10/1984 | D'Alelio |
| 5,716,625 | A | 2/1998 | Hahn et al. |
| 5,804,203 | A | 9/1998 | Hahn et al. |
| 5,824,650 | A | 10/1998 | De Lacharriere et al. |
| 5,851,556 | A * | 12/1998 | Breton ................... A61K 33/14 |
| | | | 424/617 |
| 5,866,168 | A | 2/1999 | De Lacharriere et al. |
| 6,051,609 | A | 4/2000 | Yu et al. |
| 6,623,730 | B1 | 9/2003 | Williams et al. |
| 7,404,967 | B2 | 7/2008 | Hahn et al. |
| 9,333,185 | B2 | 5/2016 | Hahn |
| 9,480,704 | B2 | 11/2016 | Hahn |
| 10,159,693 | B2 | 12/2018 | Hahn |
| 10,874,689 | B2 | 12/2020 | Hahn |
| 11,235,002 | B2 | 2/2022 | Hahn et al. |
| 11,801,261 | B2 | 10/2023 | Hahn |
| 2003/0198656 | A1 | 10/2003 | Yu et al. |
| 2004/0248942 | A1 | 12/2004 | Hepburn et al. |
| 2006/0111307 | A1 | 5/2006 | Robbins |

(Continued)

FOREIGN PATENT DOCUMENTS

| | | |
|---|---|---|
| EP | 0219455 A2 | 4/1987 |
| EP | 0273202 A2 | 7/1988 |

(Continued)

OTHER PUBLICATIONS

Ahern, et al., "Extracellular Cations Sensitize and Gate Capsaicin Receptor TRPV1 Modulating Pain Signaling", J Neuroscience, May 25, 2005; 25(21):5109-5116.

Cabrera, et al., "Beneficial Effects Of Green Tea—A Review." J Am College of Nutrition, Apr. 30, 2006, 25(2):79-99.

Cao, et al., "Intracellular Proton-mediated Activation of TRPV3 Channels Accounts for the Exfoliation Effect of a-Hydroxyl Acids on Keratinocytes", J Biol Chem. (2012), 287(31):25905-25916.

Chen, et al., "Acid mediates a prolonged antinociception via substance P signaling in acid-induced chronic widespread pain" Molecular Pain 2014, 10:30 in 5 pages.

Chen, et al., "Expression and function of proton-sensing G-protein-coupled receptors in inflammatory pain" Molecular Pain 2009, 5:39 in 19 pages.

(Continued)

*Primary Examiner* — Gina C Justice

(74) *Attorney, Agent, or Firm* — Knobbe, Martens, Olson & Bear, LLP

(57) ABSTRACT

Therapeutically-active compositions that combine strontium with at least one additional molecules that increase the overall therapeutic potency of the combination beyond the potency of any of the separate constituents. Specifically, the combinations perform two important functions; (1) they increase the ability of topically-applied strontium to inhibit both acute sensory irritation (e.g., pruritus and pain), redness, swelling and inflammation (collectively defined for purposes of this description, "irritation") and the chronic irritation that is characteristic of and contributes to the development and maintenance of painful or pruritic neuropathic conditions; and (2) they decrease the strontium activated pathways that are known to enhance the development and maintenance of pain, pruritis and neuropathic conditions.

19 Claims, No Drawings

(56) References Cited

U.S. PATENT DOCUMENTS

| | | | |
|---|---|---|---|
| 2006/0236470 A1 | 10/2006 | Sabnis et al. |
| 2007/0134232 A1 | 6/2007 | Studin et al. |
| 2008/0096872 A1 | 4/2008 | Friedman |
| 2009/0087401 A1 | 4/2009 | Hiramoto et al. |
| 2009/0131364 A1 | 5/2009 | Dharmesh et al. |
| 2009/0214628 A1 | 8/2009 | de Rijk |
| 2010/0099640 A1 | 4/2010 | Geuns et al. |
| 2010/0173021 A1 | 7/2010 | Hahn et al. |
| 2010/0226987 A1 | 9/2010 | Gnaim et al. |
| 2010/0247461 A1 | 9/2010 | Voronkov et al. |
| 2011/0129433 A1 | 6/2011 | Currie et al. |
| 2012/0255574 A1 | 10/2012 | Flohr et al. |
| 2012/0328593 A1 | 12/2012 | Huang et al. |
| 2013/0130959 A1 | 5/2013 | Li et al. |
| 2016/0250253 A1 | 9/2016 | Hahn |
| 2016/0361357 A1 | 12/2016 | Hahn |
| 2017/0049807 A1 | 2/2017 | Hahn |
| 2017/0157169 A1 | 6/2017 | Hahn et al. |

FOREIGN PATENT DOCUMENTS

| | | |
|---|---|---|
| EP | 0273202 B1 | 6/1995 |
| GB | 0487094 A | 6/1938 |
| JP | 2003-509366 A | 3/2003 |
| JP | 2004-167218 A | 6/2004 |
| JP | 2005-507396 | 3/2005 |
| JP | 2011-502505 A | 1/2011 |
| KR | 1019980700842 | 4/1998 |
| RU | 2124353 | 1/1999 |
| WO | WO 2003/028742 | 4/2003 |
| WO | WO 2006/069293 | 6/2006 |
| WO | WO 2007/000779 | 10/2007 |
| WO | WO 2013/142383 A1 | 9/2013 |
| WO | WO 2016/141219 A1 | 9/2016 |

OTHER PUBLICATIONS

Chen, et al., "Roles of ASIC3, TRPV1, and NaV1.8 in the transition from acute to chronic pain in a mouse model of fibromyalgia" Molecular Pain 2014, 10:40 in 15 pages.

Dai, et al., "Plant Phenolics: Extraction, Analysis And Their Antioxidant And Anticancer Properties." Molecules, Oct. 21, 2010, 15:7313-7352.

Du, et al., "Modulation of TRPM2 by acidic pH and the underlying mechanisms for pH sensitivity", J Gen Physiol. 2009, 134(6):471-488.

Frey-Law, et al., "Acidic Buffer Induced Muscle Pain Evokes Referred Pain and Mechanical Hyperalgesia in Humans", Pain. 2008; 140(2):254-264.

Gamper, et al., "Redox and Nitric Oxide-Mediated Regulation of Sensory Neuron Ion Channel Function", Antioxid. Redox Signal. 2015, 22(6):486-504.

Gregory, et al., "Effect of Intramuscular Protons, Lactate, and ATP on Muscle Hyperalgesia in Rats" PLOS One, 2015, 10(9):e138576 in 13 pages.

Hahn, "Strontium Is A Potent and Selective Inhibitor of Sensory Irritation" Dermatologic Surgery 25:689-694, 1999.

Hansen, et al., "Modulation of the Dimer Interface at Ionotropic Glutamate-Like Receptor 2 by D-Serine and Extracellular Calcium" The Journal of Neuroscience, Jan. 28, 2009 • 29(4) pp. 907-917.

Hasegawa, et al., "Cysteine, Histidine And Glycine Exhibit Anti-Inflammatory Effects In Human Coronary Arterial Endothelial Cells", Clin Exper Immunol. 2012, 167(2):269-274.

Huang, et al., "Acidosis Mediates the Switching of Gs-PKA and Gi-PKCε Dependence in Prolonged Hyperalgesia Induced by Inflammation" PLo One, 2015, 10(5):e0125022 in 17 pages.

Iacob, et al., "Gene expression factor analysis to differentiate pathways linked to fibromyalgia, chronic fatigue syndrome, and depression in a diverse patient sample", Arthritis Care Res. 2015, 68(1):132-140.

Jara-Oseguera et al. "TRPV1: On The Road To Pain Relief" Curr Mol Pharmacol. Nov. 2008 ; 1(3): 255-269.

Joksovic et al., "CaV3.2 is the major molecular substrate for redox regulation of T-type Ca2+ channels in the rat and mouse thalamus", J Physiol. (2006) 574(2):415-430.

Jones, "Physicochemical Properties Of Pharmaceutical Polymers", in Pharmaceutical Applications of Polymers for Drug Delivery, Smithers Rapra Publishing, Jan. 1, 2004, pp. 3-13.

Katiyar et al., "Green Tea Polyphenolic Antioxidants And Skin photoprotection." Int J Oncol., 2001, 18(6):1307-1313.

Kim et al., "Gallic Acid Inhibits Histamine Release and Pro-Inflammatory Cytokine Production in Mast Cells" Toxicological Sciences 91(1):123-131, 2006.

Lee, et al., "The calcium-sensing receptor regulates the NLRP3 inflammasome through Ca2+ and cAMP" Nature. Dec. 6, 2012; 492(7427): 123-127.

Madlener, et al., "Gallic acid inhibits ribonucleotide reductase and cyclooxygenases in human HL-60 promyelocytic leukemia cells" Cancer Letters, 245:156-162, 2007.

Meyers, et al., "The Effect Of Selected Amino Acids On Gelatin-Induced Inflammation In Adult Male Mice." Inflammation, 1979, 3(3):225-233.

Morales-Lazaro, et al., "The role of endogenous molecules in modulating pain through transient receptor potential vanilloid 1 (TRPV1)", J Physiol. 2013, 591(13):3109-3121.

Nelson, et al., "The Endogenous Redox Agent L-Cysteine Induces T-Type Ca2+ Channel-Dependent Sensitization of a Novel Sub-population of Rat Peripheral Nociceptors", J Neurosci., 2005, 25(38):8766-8775.

Nelson, et al., "Reducing Agents Sensitize C-Type Nociceptors by Relieving High-Affinity Zinc Inhibition of T-Type Calcium Channels", J Neurosci., 2007, 27(31):8250-8260.

Pae C-U., "The Potential Role of Monocyte Chemoattractant Protein-1 for Major Depressive Disorder" Psychiatry Investig. 2014; 11(3):217-222.

Pearson, The Biology Place, http://www.phschool.com/science/biology_place/bioprop/landd.html, accessed Jan. 1, 2016.

Pollak, et al., "Exogenously Applied Muscle Metabolites Synergistically Evoke Sensations of Muscle Fatigue and Pain in Human Subjects", Exp Physiol. 2014, 99(2):368-380.

Raison, et al., "Association of peripheral inflammatory markers with chronic fatigue in a population-based sample",Brain Behav Immun. 2009, 23(3):327-337.

Sansone et al., "Getting a Knack for NAC: N-Acetyl-Cysteine". Clin Neuroscience. 2011, 8(1): 10-14.

Senaldi, et al., "Protective Effect of N-Acetylcysteine in Hapten-Induced Irritant and Contact Hypersensitivity Reactions" The Journal of Investigative Dermatology, 102(6): 934-937, Jun. 1994.

Sluka, et al., "Chronic hyperalgesia induced by repeated acid injections in muscle is abolished by the loss of ASIC3, but not ASIC1", Pain. 2003, 106(3):229-239.

Sluka, et al., "The dichotomized role for acid sensing ion channels in musculoskeletal pain and inflammation", Neuropharmacol. 2015, 94:58-63.

Steen, et al., "A Dominant Role of Acid pH in Inflammatory Excitation and Sensitization of Nociceptors in Rat Skin, in vitro", J Neuroscience, 1995, 15(5):3982-3989.

Stone, et al., "Combined, but not individual, blockade of ASIC3, P2X, and EP4 receptors attenuates the exercise pressor reflex in rats with freely perfused hindlimb muscles", J Appl Physiol. (2015) 19:1330-1336.

Sugiura, et al., "Mouse colon sensory neurons detect extracellular acidosis via TRPV1", Am J Physiol Cell Physiol. 2007, 292:C1768-C1774.

Susankova, et al., "Reducing and Oxidizing Agents Sensitize Heat-Activated Vanilloid Receptor (TRPV1) Current", Mol Pharmacol. (2006), 70(1):383-394.

Todorovic, et al., "Redox Regulation of Neuronal Voltage-Gated Calcium Channels" Antioxid Redox Signal. (2014), 21(6):880-891.

Walters, "Nociceptors as chronic drivers of pain and hyperreflexia after spinal cord injury: an adaptive-maladaptive hyperfunctional state hypothesis", Frontiers in Physiology, 2012; 3:309 in 13 pages.

Wemmie, et al., "Acid-sensing ion channels in pain and disease", Nat Rev Neurosci. 2013, 14(7):461-471.

(56) References Cited

OTHER PUBLICATIONS

Yang, et al., "Lactate promotes plasticity gene expression by potentiating NMDA signaling in neurons", PNAS, 2014, 111(33):12228-12233.

Zhai, et al., "Strontium nitrate suppresses chemically-induced sensory irritation in humans" Contact Dermatitis 42:98-100, 2000.

International Preliminary Report on Patentability in corresponding International Application No. PCT/US2013/032608, dated Mar. 5, 2014.

International Search Report in corresponding International Application No. PCT/US2013/032608, dated Jun. 4, 2013.

Office Action in corresponding Australian Application No. 2013235345, dated Jun. 26, 2015.

Supplementary European Search Report in European Patent Application No. 13764092.6, dated Dec. 23, 2014.

Written Opinion in corresponding Singapore Patent Application No. 11201405866V, dated Apr. 29, 2016.

Written Opinion of the International Searching Authority in corresponding International Application No. PCT/US2013/032608, dated Mar. 21, 2012.

Japanese Office Action dated Nov. 25, 2016 for Japanese Application No. 2015-501824.

* cited by examiner

TOPICALLY ADMINISTERED STRONTIUM-CONTAINING COMPLEXES FOR TREATING PAIN, PRURITIS AND INFLAMMATION

INCORPORATION BY REFERENCE TO RELATED APPLICATIONS

Any and all priority claims identified in the Application Data Sheet, or any correction thereto, are hereby incorporated by reference under 37 CFR 1.57. This application is a divisional of U.S. application Ser. No. 17/100,652, filed Nov. 20, 2020, which is a continuation of U.S. application Ser. No. 16/189,578, filed Nov. 13, 2018, now U.S. Pat. No. 10,874,689, which is a continuation of U.S. application Ser. No. 15/284,892, filed Oct. 4, 2016, now U.S. Pat. No. 10,159,693, which is a continuation of U.S. patent application Ser. No. 14/493,202, filed Sep. 22, 2014, now U.S. Pat. No. 9,480,704, which is a divisional of U.S. patent application Ser. No. 14/386,731, filed Sep. 19, 2014, now U.S. Pat. No. 9,333,185, which is the U.S. National Phase of International Application No. PCT/US2013/032608, filed Mar. 15, 2013, which claims the benefit of U.S. Provisional Application No. 61/613,923, filed Mar. 21, 2012. Each of the aforementioned applications is incorporated by reference herein in its entirety, and each is hereby expressly made a part of this specification.

TECHNICAL FIELD

The present disclosure consists of therapeutically-active compositions that combine strontium with at least one additional molecules that increase the overall therapeutic potency of the combination beyond the potency of any of the separate constituents. Specifically, the combinations described herein perform two important functions; (1) they increase the ability of topically-applied strontium to inhibit both acute sensory irritation (e.g., pruritus and pain), redness, swelling and inflammation (collectively defined for purposes of this description, "irritation") and the chronic irritation that is characteristic of and contributes to the development and maintenance of painful or pruritic neuropathic conditions; and (2) they decrease the strontium activated pathways that are known to enhance the development and maintenance of acute pain and pruritis, and neuropathic conditions.

BACKGROUND OF THE INVENTION

U.S. Pat. No. 5,716,625 describes the ability of topically-applied strontium, in divalent ionic form, to rapidly suppress acute sensory irritation (e.g., stinging, burning pain and/or itching) and accompanying inflammation due to chemical irritants, electromagnetic radiation, "environmental irritants" and diseases (strontium's "anti-irritant activity").

While not being bound or otherwise limited by any particular biochemical mechanism, it was theorized that strontium's anti-irritant activity was due to the ability of strontium to selectively suppress activation of Type C Nociceptors (TCN), the only sensory nerves that produce and transmit stinging, burning pain and itching sensations and the neurogenic inflammatory response that can accompany TCN activation.

When compared to the existing topical drugs able to suppress such sensory irritation like lidocaine or Novocain™, the local anesthetic typically used by dentists during dental procedures, strontium has a unique property—it is highly selective for only the TCN and doesn't significantly affect the many other sensory nerves that provide normal tactile sensations and "cutaneous awareness." Since lidocaine and other topical local anesthetics lack this specificity for TCN, they can cause numbness and loss of function.

While topically applied strontium can rapidly inhibit the activation of TCN sensory nerve subsets that transmit sensations of pain (e.g., burning and stinging) and pruritus (itching), recent investigations to understand strontium's anti-irritant mechanisms surprisingly reveal that strontium also has negative effects on several biochemical pathways that tend to negate the positive anti-irritant benefits of strontium for treatment of neuropathic conditions.

Therefore it is desirable to create new strontium-containing molecules, complexes and formulations that increase the "positive" therapeutic benefits of strontium and decrease the "negative" effects of strontium on acute pain, pruritis and neuropathic conditions

SUMMARY OF THE INVENTION

In accordance with the teachings herein, the present disclosure relates generally to compositions of strontium-containing complexes in a suitable carrier vehicle.

The complexes are bipartite or tripartite in nature, in that they include at least one or two different components: divalent cationic strontium, and at least one counterion, such as a polyhydroxyphenol or an aromatic amino acid. In the form of a tripartite composition, the complexes include divalent cationic strontium, at least one polyhydroxyphenol, and at least one cysteine-based antioxidant.

The cysteine-based anti-oxidant may be selected from the group consisting of: cysteine, cystine, N-acetyl cysteine (NAC), N-acetyl cysteinate, N-acetyl cystine and N,S-diacetylcysteine, or mixtures thereof.

In addition, the polyhydroxyphenol may be selected from the group consisting of: gallic acid, caffeic acid, quercetin, luteolin, epigallocatechin gallate, epigallocatechin, epicatechin gallate, genistein and myricetin, or mixtures thereof. In one embodiment the polyhydroxyphenol is a mixture of gallic acid and caffeic acid.

Either the bipartite or tripartite complexes may also be complexed with a polymer, such as a polyanionic polymer. This polymer may be selected from the group consisting of: polyvinylpyrrolidone (PVP), cyclodextrins, carragenans, alginic acid, xanthan gum, sulfated polysaccharides, pentosan polysulfate, chondroitin sulfate, dextran sulfate and heparin sulfate.

The osmolarity of the compositions may beneficially have high osmotic activity, such as having an osmolarity equal to or greater than 400 mOsm, or between 400 and 2000 mOsm.

The polyhydroxyphenol(s) is(are) in essentially pure form when added to the compositions described herein, or is(are) added in the form of a plant extract, such as green tea or soy extract.

In an alternate embodiment of a tripartite composition, the at least one cysteine-based anti-oxidant and the at least one polyhydroxyphenol are conjugated together by a cleavable bond, such as a peptide bond, an ester bond, a thioester bond, an enzymatically cleavable bond, a disulphide bond, or a pH dependent bond.

In an alternate embodiment of a bipartite composition, the divalent cationic strontium is complexed with at least one polyhydroxyphenol (as described above), and the complex is placed in a suitable carrier vehicle prior to administration.

In yet another embodiment of the bipartite composition, the divalent cationic strontium is complexed with an aromatic amino acid, and the complex is placed in a suitable carrier vehicle prior to administration. Such amino acids include, for example, histidine, tyrosine, phenylalanine and tryptophan, and are in one embodiment in the L isomer form.

The compositions containing bipartite complexes can also include other constituents, such as any of the aforementioned strontium counterions.

Other aspects of the invention are found throughout the specification.

DETAILED DESCRIPTION OF THE INVENTION

The present disclosure consists of therapeutically-active compositions that combine strontium with at least one additional molecules that increase the overall therapeutic potency of the combination beyond the potency of any of the separate constituents. Specifically, the combinations described herein perform two important functions; (1) they increase the ability of topically-applied strontium to inhibit both acute sensory irritation (e.g., pruritus and pain), redness, swelling and inflammation (collectively defined for purposes of this description, "irritation") and the chronic irritation that is characteristic of and contributes to the development and maintenance of painful or pruritic neuropathic conditions; and (2) they decrease the strontium activated pathways that are known to enhance the development and maintenance of acute pain and pruritis, and neuropathic conditions.

Accordingly, the present disclosure relates, in part, to compositions that include complexes of divalent strontium, and at least two counterions—a cysteine based anti-oxidant and a polyphenolic compound, both of which are discussed in greater detail below.

Another aspect of the present disclosure relates to compositions that include complexes of divalent strontium and at least one polyhydroxyphenolic compound.

In yet another aspect of the present disclosure relates to compositions that include complexes of divalent strontium and at least one amino acid.

In the description that follows, a number of terms are extensively utilized. In order to provide a clear and consistent understanding of the specification and claims, including the scope to be given such terms, the following non-limiting definitions are provided.

When the terms "one," "a," or "an" are used in this disclosure, they mean "at least one" or "one or more," unless otherwise indicated.

The term "skin" refers to external surfaces of the body in the broadest sense of the word and therefore implicitly includes all keratinized skin as well as, for example, the epithelial surfaces of the eye, the respiratory tract, the gastrointestinal tract and the genitourinary tract, including the cervix and the vagina.

The term "salt" as used herein refers to the common chemical definition of salt—that is, a compound that is composed of ionic, charged substances (atoms and/or molecules) that combine to form an electrically neutral compound having no net electrostatic charge.

The term "complex" as used herein refers to a combination of the strontium cation and two other negatively charged or polar molecules (strontium counterions) via either electrostatic forces (for example, due to the pi-electrons in the phenolic ring structures), or association with a partial negative charge or other inter-molecular charges. In addition to strontium and the two strontium counterions, the complex may also contain polymeric substances like polyvinylpyrrolidones, polyacrylamides, polyanionic polymers like alginic acid, carrageenans or carbohydrate polymers that have an inherent ability to reversibly bind to and complex with thiol-containing molecules like N-Acetyl-L-Cysteine (NAC), or polyhydroxyphenolic compounds like gallic acid, quercetin, leuteolin, myricetin and other similar molecules.

The term "cysteine-based" anti-oxidant as used herein refers to cysteine, cysteine derivatives, cysteine-containing small (less than four amino acids) peptides and cysteine precursors.

The term "cleavable" means a covalent chemical bond that is capable of being broken. "Cleavable" only requires that a fraction of the chemical bonds are cleaved, that is, the chemical bonds are cleavable if a portion of the bonds are cleaved. In one instance, the bond is cleavable within the skin after administration.

The term "conjugated" means a compound where at least two of the components are joined together with a cleavable bond.

The term "neuropathic" as used herein is used interchangeably with "chronic", and includes neuropathic pain, neuropathic pruritis, and neuropathic itching. It is recognized that neuropathic conditions are typically accompanied by nerve damage. Exemplary neuropathic conditions include, for example, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central post-stroke pain, multiple sclerosis pain, parkinson disease pain and spinal cord injury pain.

Other pain-associated terminology may include the following:

TABLE I

| Pain Term | Definition |
|---|---|
| Allodynia | Pain due to a stimulus that does not normally provoke pain |
| Analgesia | Absence of pain in response to stimulation that is normally painful |
| Hyperalgesia | An increased response to a stimulus that is normally painful |
| Hyperesthesia | Increased sensitivity to stimulation, excluding the special senses |
| Hyperpathia | A painful syndrome characterized by an abnormally painful reaction to a stimulus, especially a repetitive stimulus, as well as an increased threshold |
| Hypoalgesia | Diminished pain in response to a normally painful stimulus |
| Hypoesthesia | Decreased sensitivity to stimulation, excluding the special senses |

Strontium's Anti-Irritant & Anti-Inflammatory Activity Can Be Greatly Enhanced

It has been surprisingly discovered that the reason strontium is frequently unable to completely block pain, itching or inflammation is due to two factors: (1) the limited amount of strontium that can be topically applied, after which the hyperosmotic effects of the strontium salts themselves start to cause pain, itching or inflammation. This is due to the fact that strontium has a relatively low potency in its ability to suppress pain, itching and inflammation compared to many other drugs with similar therapeutic goals; and (2) the ability of strontium to stimulate pathways that may act to negate strontium's inherent anti-irritant activities, thus reducing the overall therapeutic benefit. The degree to which strontium will negate its anti-irritant benefits depends on many factors related to the type of nerve damage that caused the neuropathic condition to develop (e.g., viral infection, physical trauma such as amputation or nerve compression, metabolic nerve damage as occurs in diabetes, coexisting inflammation and other factors.

For example, commonly used non-steroidal anti-inflammatory drugs (NSAID) like aspirin, ibuprofen and naproxen are typically used at oral doses of several hundred milligrams and provide an effective reduction of many types of inflammation-associated pain. Opioid pain relievers such as levorphanol, oxymorphone, oxycodone and hydrocodone are pharmacologically related to codeine, morphine and heroin and provide effective pain relief at oral doses in the range of 2 mg to about 10 mg per dose. In contrast, orally administered strontium salts such as strontium ranelate, an oral drug approved for the treatment and prevention of osteoporosis, is approved in over 70 countries, and is administered at a dose of 2,000 mg per day. Since strontium ranelate is a simple salt of strontium, it yields 680 mg of elemental strontium upon contact with water or gastric fluids. However, even at this high dose of pure elemental strontium, there are no reports of the ability to reduce pain or inflammatory reactions.

It has been determined that topical strontium has the ability to reduce pain, pruritus and inflammation due to the fact that topical formulations can deliver thousands of times higher strontium concentrations then can be achieved by oral, systemic administration. Even at the relatively high local concentrations that can be achieved topically when administered to the skin, the effect of strontium on key biochemical pathways that cause pain, pruritus and inflammation is only partial. For example, if the activity of a hypothetical pain or itch-producing pathway is inhibited by 90% to 100%, a patient reports that their pain or itching was completely stopped. In contrast, topically-applied strontium may only inhibit that pathway by 40% to 50%, sufficient inhibition for a patient to observe that the pain or itching was clearly reduced, but still present and still bothersome.

The Skin Senses Danger by Activation of Multiple Molecular Sensors

The skin senses potentially harmful chemicals by two classes of nerves, called nociceptors, that form a "sensory web" just under the surface of the skin. A-delta nerves respond to physical trauma by transmitting a pain sensation with a sharp, pricking quality. Type C nerves (TCN) are chemical sensors that respond to irritants from our environment, microbes, temperature extremes, ionizing radiation and allergic and non-allergic skin conditions and transmit diffuse sensations of burning, stinging pain or itching ("irritation"). When excessively stimulated, TCN can also release neuropeptides (e.g., Substance P) that directly activate histamine-containing mast cells and attract and activate other immune system cells such as neutrophils that cause redness, swelling and even local skin damage. After activation by irritant triggers in the skin, both nociceptors synapse near the spinal cord in the dorsal root ganglia (DRG) and release neurotransmitters that activate nerve pathways that relay signal to the brain where the irritant quality of the sensations is consciously appreciated.

Acute, Chronic & Neuropathic Pain & Pruritus Occur Upon Nociceptor Activation

Upon activation, both types of nociceptors may be activated or in many instances either the A-delta or TCN are preferentially activated. Since only the TCNs extend to the outermost portions of the epidermis and may be activated by virtually any process that changes the local biochemistry of the epidermis, TCNs are preferentially activated in response to most irritating stimuli. Upon activation of TCNs in the skin, the TCNs transmit a signal to the spinal cord and trigger neurotransmitter release in the DRG that activate nerves in the spinal cord that relay the pain and itch signals to the brain. Acute activation of TCNs that is caused by exposure to a chemical irritant, trauma or a sunburn typically causes painful or pruritic sensations that last only several days and is termed "nociceptive pain". When the stimulus is prolonged or excessively severe as can occur after a viral disease like shingles or HIV, or the nerves are damaged by trauma to nerves from physical pressure, thermal bums, diabetes or extensive physical trauma to a limb, painful sensations or pruritus can continue for many years. Such chronic pain or pruritus caused by excessive nociceptor activation or damage is termed "neuropathic" and is among one of the most difficult conditions to treat. Even the best oral or topical drugs have only a very limited therapeutic benefit and many have substantial side effects that limit their use.

Nociceptive Signals are Typically Encoded as Precisely-Timed Changes of Intracellular Calcium Concentration that Travel as "Calcium Waves" within Nociceptors No matter what causes nociceptor activation, the event is encoded into a universal code; a complex change in the intracellular calcium concentration that, in tum, is transmitted throughout the nociceptor. Calcium thus acts as a universal "second messenger" and information transmitted by a nociceptor, including the intensity and quality of pain or pruritus is converted into a language made up of rapidly changing calcium concentrations. Since nerves in general and nociceptors in particular transmit their calcium code typically within about $\frac{1}{1000}$th of a second, the timing and spatial distribution of calcium must be exquisitely regulated to accurately transmit the encoded information. In virtually all nerves, including nociceptors, the intensity of the signal (e.g., the severity of pain or pruritus) is encoded as a change in frequency of neurotransmitters that are released into the synapse and activate post-synaptic nerves that relay the information ultimately to the brain. The higher the frequency, the more intense the perceived sensation. When a nociceptor is activated, the calcium signal is transmitted through multiple biochemical pathways, many of which operate in sequence such that the output of one pathway becomes the input of the next.

Nociceptive Signals and the Biochemical Pathways that Encode Signals Have an Output that is Logarithmically Related to the Input The many nociceptor pathways as well as the overall neurotransmitter release by a nociceptor is typically logarithmically related to the intensity of the stimulus. For example, if the irritant caused the nociceptor activation to increase its frequency of activation, also called depolarization, from 10 to 50 per second, the frequency of the resultant neurotransmitter release may only increase by a factor of 1.7 (Log 10=1.0; Log 50=1.7). This fact is particularly relevant since it suggests that a relatively small amount of inhibition of a nociceptor's activation can cause a large reduction in the perceived severity of the painful or pruritic stimulus. Since there are many separate pathways in nociceptors that act in sequence to encode and transmit the irritant stimulus, inhibiting each of the sequential pathways at one or more of a pathway's steps has the potential to produce a very large cumulative reduction of the painful or pruritic sensation.

Current strontium-containing formulations typically use strontium nitrate or strontium chloride hexahydrate as the strontium source. Since neither the nitrate or chloride anions contribute to strontium's ability to reduce pain or pruritus, they only act to increase the osmolarity of the formulation. Recent research has demonstrated that high osmolarity formulations activate specific osmotic sensors present on nociceptors, keratinocytes and immune or inflammatory cells that can activate nociceptors. An example of this is the "salt in the wound" effect that causes stinging and burning if a concentrated solution of a simple salt is poured into wound. In addition to causing discomfort, high osmolarity solutions can directly activate inflammatory cells and cause them to release chemicals that cause nociceptor activation. It is therefore desirable to eliminate as many "non-active" components of the strontium salt or complex to minimize the potential for osmotic-induced nociceptor activation and inflammation.

Strontium Alters the Dynamics and Spatial Distribution of Calcium Waves

Strontium's unique therapeutic properties are due to its chemical resemblance to calcium, the most important and universal "second messenger" in nerves and in all other cells that regulate virtually all cellular functions. The calcium ion always has two positive charges and its ionic radius is 0.99 angstroms, about the size of a hydrogen atom. Of all the elements, strontium most closely resembles calcium, since it also only exists as a divalent positively charged ion and has an ionic radius of 1.13 angstroms. For this reason, strontium typically binds to calcium-binding sites and mimics calcium's activity. Most often a strontium-induced response is less potent and may be as low as about 1/1000th as active as calcium, but more often, strontium has activity that is nearly the same as calcium or in the range of 1/10th to 1/30th as active as calcium. In other calcium-dependent activities, strontium can be more active than calcium, for example. It is strontium's calcium-mimetic activity that enables strontium to produce its many and varied activities. Since calcium is critical for so many cellular functions, if it were strongly inhibited the effects would be toxic to a cell. In contrast, since strontium can typically substitute for calcium, albeit with lower activity, the activity of the calcium-dependent pathway will not be shut down. Instead, the pathway activity will be reduced, similar to turning down the volume control of a radio. Since strontium, in a metaphoric sense, only turns down the volume control of calcium-dependent pathways rather than shutting down such pathways, the chances of significant adverse reactions or toxicity is much reduced compared to a drug that completely blocks a pathway.

When irritants from chemicals, disease, trauma or other exposures activate receptors on the surface of TCNs that encode the intensity of their response as rapid changes in intracellular calcium concentrations, these changes can occur in less than 1000th of a second and produce highly complex "waves" of changing calcium concentration that propagate through the nerve and trigger most, if not all, of the pathways that cause acute, chronic and neuropathic irritation. In addition to the frequency of calcium waves, alterations in the dynamics of calcium concentration change the duration, magnitude and the precise shape of the calcium waveform that alters the coexisting electrostatic field that is a critical regulator of TCN activity. These changes independently activate the release of multiple inflammatory mediators, including prostaglandins (e.g., PGE2), leukotrienes (e.g., LTB4, C4, D4 & E4) and reactive oxygen species (ROS) including superoxide, hydrogen peroxide, hydroxyl radicals, hypochlorous acid and peroxynitrite.

Strontium thus significantly alters the pain and itch sensations encoded within calcium waves present in painful and pruritic neuropathic conditions, and has the effect of garbling the signal and reducing its perceived intensity by the brain. Due to strontium binding to multiple calcium-dependent signaling pathways, strontium significantly alters calcium-encoded signals by multiple independent mechanisms. Some of the calcium-dependent kinases are known to be essential for the development of neuropathic conditions, since their inhibition in animal models can prevent and or reverse established neuropathic conditions.

Strontium is not able to bind effectively to the calcium binding proteins within the cytoplasmic interior of nociceptors that normally remove calcium within less than a millisecond after calcium enters the nociceptor, thus producing a transient increase in calcium concentration that contributes to the precisely-timed calcium waves. Strontium is also much less effectively pumped into and released from a nociceptor's primary calcium storage site, the endoplasmic reticulum (ER). When a nociceptor-activating signal is received, strontium inhibits the calcium-induced calcium release (CICR) pathway that amplifies the calcium signal, and strontium does not have the ability to regulate inositol triphosphate (IP3)-induced calcium release by acting to inhibit additional calcium release if the concentration of calcium in the cytoplasm is too high.

Once calcium enters a nociceptor during its activation and depolarization, it activates the release of a massive amount of calcium that is stored in the ER by the CICR pathway. This mechanism has the effect of greatly amplifying the amount of calcium that is available to form a wave and to regulate calcium-dependent pathways. Strontium is over a hundred-fold less active than calcium in its ability to induce CICR and thus significantly alters the calcium concentration changes that normally occur in response to irritants. When in the ER, strontium also binds much less avidly to the ER calcium binding proteins that act as buffers and sequester the free calcium until it is released by CICR or other similar mechanisms. As a result, strontium reaches a concentration of more than 150% greater than calcium and displaces calcium from performing its amplifying function during CICR. Strontium is also much less active then calcium in regulating a second important calcium amplifying mechanism triggered by IP3, a ubiquitous substance that also activates calcium release from the ER by an IP3—specific receptor. At low concentrations of calcium, IP3 acts as a potent stimulator of calcium release that acts to amplify the much smaller calcium influx during depolarization. When the calcium concentration is sufficiently elevated, calcium acts to inhibit further calcium release thus maintaining the calcium concentration within a limited concentration range. When strontium is present, it can mimic calcium in its ability to activate IP3—induced calcium release, but strontium is not able to inhibit excessive calcium release causing both calcium and strontium to reach higher concentrations over an extended time. Strontium's ability to completely inhibit calcium-induced release due to IP3 is particularly important, since IP3-induced calcium release is known to be responsible for generation of calcium waves. These types of strontium effects significantly change the calcium dynamics and calcium waveforms associated with neuropathic conditions, and thus contribute to strontium's suppressive effects on pain and pruritis.

Strontium Inhibits Calcium-Dependent Neurotransmitter Release

While strontium also affects additional pathways that control the dynamics of calcium within nociceptors, there is one strontium-induced interference with calcium-dependent transmission of pain and itch-encoded calcium waves that is critically important for suppression of both acute, chronic and neuropathic conditions. That is, the ability of strontium to bind and inactivate synaptotagmin-1, a molecule that is principally responsible for neurotransmitter release in the DRG and release of inflammatory neuropeptides, including substance P from the peripheral portion of a TCN in the skin. Substance P is known to be the most important inflammatory neuropeptide released from TCNs that activates virtually every inflammatory immune "white blood cell" (WBC), including mast cells that contain histamine and over 50 different inflammatory chemicals, including Tumor Necrosis Factor-alpha (TNF-alpha), Interleukin 1 alpha and beta (IL-1 alpha & beta) and IL-6. These three pro-inflammatory cytokines are believed to be the "first responders" that directly activate TCNs to cause pain and/or itching and are thought to be significant contributors to the development and maintenance of neuropathic conditions, as well as most skin conditions that are associated with inflammation, pain or itching.

Synaptotagmin-1 is a protein present on the surface of vesicles that contain and ultimately release neurotransmitters and anti-inflammatory neuropeptides like substance P from the pre-synaptic endings that bind to the post-synaptic neurons in the DRG and the peripheral TCN endings in the skin that relay the pain and itch-encoded signals to the brain. Normally, the frequency of the presynaptic neurotransmitter release from nociceptors are precisely matched so that the intensity, timing and other properties of the original pain or itch signal encoded in the calcium wave is accurately transmitted to the brain. The delay between the arrival of the calcium wave, neurotransmitter release and post-synaptic activation is usually about 1000th of a second and the amount released is related to the intensity of the original TCN signal. This type of neurotransmission is termed "synchronous release," since the timing of the arrival of the calcium wave is tightly synchronized to the release of neurotransmitters that trigger post-synaptic activation of the DRG nerve. Without this precise coupling, the frequency encoded pain or itch signal becomes distorted and garbled.

When strontium substitutes for calcium, the amplitude of synchronous neurotransmitter release in response to TCN activation is typically reduced by more than 90%. Strontium has an additional signal distorting effect that significantly distorts the timing of neurotransmitter release called "asynchronous release." In contrast to synchronous release that is tightly coupled to the stimulating signal, asynchronous release may extend to several hundred milliseconds. With strontium, the total amount of neurotransmitter that is released may be the same as with calcium, however the strength of the synchronous release that contains the encoded pain or itch intensity information is strongly reduced, and the critical timing information is essentially destroyed. This strontium mechanism not only reduces the perceived severity of a pain or itch signal, but it also suppresses the release of substance P at the proximal end of the TCN in the skin at the original site of TCN activation. Strontium's ability to inhibit the release of TNF-alpha, IL-alpha and IL-6 from keratinocytes is probably due to the same synaptotagmin-induced release mechanism since it is the secretory mechanism used by virtually every cell. Suppression of synchronous neurotransmitter release also has an important therapeutic benefit for neuropathic pain or pruritus treatment.

Accordingly, in one embodiment, it is therefore desirable to further alter the calcium dynamics of nociceptors by further suppressing calcium release or by interfering with critical calcium-dependent pathways that are partially inhibited by strontium.

The Development and Maintenance of Neuropathic Pain or Pruritus Requires Excessive and Continuous Nociceptor Activation In order for a neuropathic condition to develop, nociceptors must be continuously activated by a potent stimulus. The duration of the activation required may substantially vary depending on the specific nerve injury or stimulant. When such activation occurs, the peripheral nociceptors that innervate the skin and mucous membranes may become sensitized within hours and may continue to increase their sensitivity to irritants and may even be activated by stimuli that are normally not irritating. Infections such as HIV or Herpes viruses, or chronic colonization by bacteria such as *Staphylococcus aureus* that is present at excessive levels on the skin of atopic dermatitis patients, bum patients, patients suffering from ionizing radiation or traumatic damage to a nerve are especially potent nociceptor sensitizers. Release of multiple inflammatory mediators that accompany any trauma or inflammation are also important contributors to sensitization.

In order to establish a neuropathic state, sensory nerves in the DRG that receive sensory input from the TCN must also become sensitized. As for the peripheral TCN, the central neurons require sustained, high intensity activation for an extended period of time that may be as short as several weeks or much longer. The presence of inflammation, infectious agents, or trauma can accelerate the sensitized, neuropathic state. Due to neuronal "cross-talk," it is common for an initially small painful portion of sensitized skin, for example, as occurs in postherpetic neuralgia, to expand to the adjacent skin via nociceptors that were uninjured, including A-delta nociceptors. Sensitized neuropathic skin may also generate painful stimuli in response to mechanical pressure or temperature changes, a condition known as allodynia.

The sensitized state in both the peripheral nociceptors and their central counterparts is a form of activity-dependent plasticity that is very similar to the neurons in the CNS that form memories. In the case of neuropathic pain or pruritus, the nociceptive response produces a "memory of pain or itching". The molecules and pathways that produce the long lasting neuronal sensitization are reasonably well defined. In particular, the activation of intracellular kinases. Of particular importance are Protein Kinase A and C (PKA & PKC), each of which exist in several different forms—the Mitogen Activated Protein Kinases (MAPK) that include the p38 MAPK, ERKI/2 MAPK and the JNK MAPK. These kinases are activated by a broad range of environmental "danger signals" and internal cytokines and growth factors exposures including ionizing radiation, reactive oxygen species (ROS) always accompany infection and trauma. When activated, these kinases are activated in multiple pathways and give rise to sequential cascades that result in regulation and activation of genes that regulate well over 100 different molecules that activate immune cells, produce inflammation and molecules that influence ion channels, and molecular sensors that cause the peripheral and central nociceptor sensitization that causes neuropathic pain and pruritus. Among these inflammation and immune system activating genes, the most important is called Nuclear Factor, Immunoglobulin Light Chain Kappa, Enhancer of B Cells, abbreviated NF-Kapa B, called the "Master Regulator of Inflammation". Additionally, some of these kinases like PKC can directly sensitize and activate nociceptors that cause calcium influx and interfere with strontium's ability to alter the calcium dynamics that occur in neuropathic states.

Accordingly, in one embodiment, it is therefore desirable to combine strontium with molecules that inhibit one or more of these kinases and regulatory genes that contribute to nociceptor sensitization, activation and generation of neuropathic conditions.

Strontium Binds to a Calcium-Sensing Receptor (CaSR) on Nociceptors that Suppresses Nociceptor Activation Most, if not all, cells have a recently-identified surface receptor that detects the extracellular calcium concentration. Strontium also binds and activates the CaSR as efficiently as calcium, but triggers additional activities. This knowledge resulted in the commercial development of a simple strontium salt, strontium ranelate, an orally administered prescription drug for osteoporosis treatment in over 70 countries. Due to strontium's unique ability to mimic calcium's ability to activate the CaSR and, additionally, to activate additional pathways linked to the CaSR, strontium ranelate is the only known osteoporosis drug that has two independent osteoporosis therapeutic mechanisms—strontium inhibits bone loss by inhibiting bone-resorbing osteoclasts, and simultaneously stimulates osteoblasts that produce new bone.

Nociceptors also have a CaSR that inhibits nociceptor activation when the extracellular concentration of calcium is raised above normal, or if a similar concentration of strontium is administered. This mechanism contributes to the ability of strontium to rapidly inhibit TCN activation by, for example, highly acidic chemical peels such as 70% glycolic acid, pH 0.6, that cause burning pain within seconds after application. When strontium is mixed with the acid, burning pain and stinging is suppressed by 80% or more so that any remaining sensory irritation is not bothersome.

Activation of the CaSR also causes activation of several pathways that are known to increase both acute, chronic and neuropathic pain and pruritus and inflammation. Since in real world use, strontium typically inhibits pain and pruritus, it is likely that the pain and itch enhancing effect caused by activation of the CaSR by strontium is, in effect, negated by other strontium anti-irritant mechanisms. None the less, even a low level, "subclinical" pain and itch enhancing effect reduces the ability of strontium to effectively treat, prevent or reverse neuropathic conditions for which any excess TCN activation is known to promote the neuropathic condition.

Of particular concern is strontium's reported ability to bind to the CaSR and rapidly activate two of the MAPK molecules, p38 and ERKI/2, that are known to be among the primary contributors to peripheral and central nociceptor sensitization. Strontium binding to the CaSR is also reported to activate an important enzyme, Phospholipase C, that produces two important regulatory molecules, the aforementioned IP3, and diacylglycerol (DAG), both of which contribute to nociceptor activation and sensitization and inflammation. IP3 is one of the most important and potent calcium releasing molecules that directly triggers calcium release from ER stores. Many of the pain and itch producing chemicals that are produced during inflammation, infection or trauma use the IP3 pathway to activate nociceptors and produce the calcium waves that transmit pain and itch sensations. DAG is the principle activator of Protein Kinase C, a family of molecules that directly activates nociceptors and many of the pathways that produce pain and itch and inflammatory mediators. PKC is also known to be an important nociceptor sensitizer, since PKC inhibition can prevent or reverse neuropathic pain in animal models. PKC also activates NF-Kappa B, one of the most important stimulators of molecules that trigger pain, pruritus and inflammation and are thought to be able to directly cause neuropathic sensitization. It should be emphasized that the recognition that strontium produces its osteoporosis therapeutic benefits by binding to the CaSR is very recent and additional strontium sensitive pathways will likely be identified. The fact that human nociceptors have the CaSR that regulate nociceptor activation suggests that the CaSR activation by topically-applied strontium may be working at a reduced level due to strontium's ability to inhibit important pain and itch pathways while simultaneously activating pathways via the CaSR that are known to trigger pain and itch pathways. Most importantly, since activation of these CaSR pathways are known to be important contributors to the development of neuropathic conditions, strontium's therapeutic potential may be substantially compromised.

Accordingly, in one embodiment, it is therefore desirable to create strontium-based salts, complexes or formulation that have molecular components that specifically inhibit the CaSR pathways known to enhance neuropathic pain, pruritus and inflammation.

The Primary Goals of the Present Disclosure

It is one object of the present disclosure to inhibit multiple nociceptor pathways by combining strontium with other molecules that specifically target pathways that are regulated by strontium and produce an overall reduction in pain or pruritus or other benefits to a patient, such as preventing or reversing a neuropathic pain or pruritic condition. It is another object of the present disclosure to combine strontium with other molecules that also cause inhibition or stimulation of strontium regulated pathways, but a different step than those regulated by strontium. It is important to note that some nociceptor pathways are inherently inhibitory and if inhibited, the overall result may be stimulation of the nociceptor. For this reason, the term "strontium-regulated pathway" will be used to denote the fact that the overall effect of strontium or the molecules that are to be combined with strontium may either stimulate or inhibit a particular nociceptor pathway. It is another object of the present disclosure to combine strontium and additional molecules in a chemical manner that causes strontium and the molecules to chemically combine as a "salt" or "complex," for example a high molecular weight polymer such as polyanionic polymers such as alginic acid, carrageenan or other polymers that can form a matrix with strontium and the additional strontium-regulating molecules. By creating strontium salts or complexes, the osmolarity of a formulation will be reduced in comparison to having a strontium and two inactive counterions to balance strontium's two positive charges.

Since it was first described in U.S. Pat. No. 5,716,625 that there is an inherent ability of the strontium ion to selectively suppress stinging, burning pain and itching and associated redness caused by chemical irritants and by diseases, referred to as its "anti-irritant activity" it was a goal to try to understand how strontium was accomplishing this activity with the aim of combining strontium with one or more unrelated molecules that amplify the biochemical pathways affected by strontium and thus produce a more potent therapeutic useful for treating many serious conditions and diseases for which current treatments have significant efficacy or safety limitations and for which strontium was not sufficiently potent. The results of this effort revealed an extraordinarily complex combination of strontium-induced regulatory effects that were able to predict the observed therapeutic profile of strontium. Most importantly, this understanding suggested how to design new strontium-based compounds, complexes and formulations that effectively treat pain and pruritus due to nerve damage, conditions generically termed "neuropathic".

There are many causes of neuropathies, some of which are very common. For example, common neuropathies include viral infection (e.g., HIV, the Herpes varicella zoster virus (VZV) that causes chicken pox and in later years, or secondary to immunosuppression, shingles and for many, post-herpetic neuralgia, an intensely painful condition that typically occurs in advanced age.) Diabetes is the most common cause of the typical burning pain due to glucose-induced nerve damage, serious burns, severe trauma or amputation and a number of drugs, especially some that are used to treat HIV. While there are oral drugs available like gabapentin (Neurontin™) and pregabalin (Lyrica™) that can provide significant relief from neuropathic symptoms, they all have potentially significant side effects such as somnolence, dizziness and changes in mentation in more than 25% of patients. Since many neuropathic patients are in their 70s or 80s and already have health limitations, these side effects can be particularly problematic and potentially dangerous. This frequently leads to reduced compliance with the required dosing schedule and thus reduced patient benefit.

It is a particularly important object of the present disclosure to create effective topical drugs, complexes and formulations that are sufficiently safe to be used as needed and without fear of medically significant side effects, and that can effectively treat pain and pruritus caused by neuropathic conditions. It is also an object of the present disclosure to prevent the development of the chronic nerve changes that produce the neuropathic state and to significantly reverse the underlying biochemical changes that produced the neuropathic condition so that the patient experiences a greatly reduced level of pain or pruritus. For some types of neuropathic conditions, the nerve changes and damage may be sufficiently reduced to the point where the patient is no longer bothered by pain or pruritus.

Accordingly, the complexes and formulations of the present disclosure enhance strontium's ability to treat neuropathic conditions, and generally achieve the following goals:
1. Stimuli that Oxidize Intracellular Glutathione Trigger Multiple Nociceptor-Activating Pathways Of the many conditions that may cause nociceptor activation during the development of neuropathic conditions, the redox state of a nociceptor can produce some of the most potent acute and chronic nociceptor activating stimuli that exist. One of the most important regulatory signals that cause a cell to convert to a defensive state in which multiple inflammatory and cell protective immune activators are activated is the intracellular ratio of reduced to oxidized glutathione. Glutathione is the most plentiful intracellular thiol antioxidant, and is among the most important signal generators that trigger a cell to synthesize powerful inflammatory mediators and activate genes that, in turn, activate virtually every immune system inflammatory cell. The ratio of reduced glutathione, GSH, to the oxidized form, GSSH, is normally 9 to 1 or more. When cells are exposed to trauma, infection, inflammation or inflammatory mediators, ionizing radiation or general "cellular stress," the amount of reduced glutathione plummets and directly triggers multiple cascades of gene activation that ultimately lead to the synthesis of well over 100 inflammatory mediators, pro-inflammatory cytokines (e.g., TNF-alpha, IL-1, IL-6 and many others), and cytokines that attract and active inflammatory immune cells, all of which sensitize and activate nociceptors that transmit pain and pruritic signals, and in turn amplify these inflammatory cascades by neurogenic inflammatory pathways. Many of a cells most important regulators of inflammation and immune defense are highly sensitive to a reduction in a cell's GSH concentration, and are directly activated by a low GSH/GSSG ratio indicating that a cell is in an oxidative redox state.

Perhaps the most important of these redox-sensitive regulatory pathways is NF-Kappa B. This molecule is responsible for that directly or indirectly inducing the synthesis of among the most important and powerful inflammation activators, including TNF-alpha and many of the inflammatory interleukins and chemokines that attract inflammatory cells that secrete mediators that directly activate nociceptors and thus increase their long-term sensitization and conversion to a neuropathic state.

Since NF-Kappa B acts as a "final common pathway" for activation of multiple inflammatory pathways, substances that reduce or block NF-Kappa B activation will have substantial and broad anti-inflammatory activity and will block many forms of immune system mediated activation of inflammatory pathways.NF-Kappa B is also one of the many regulatory molecules that is directly activated by an oxidative intracellular environment—one in which the ratio of reduced glutathione (GSH) to oxidized glutathione (GSSG) is minimized. This oxidative environment directly activates NF-Kappa B that greatly increases the synthesis of nociceptor-activating mediators and cytokines.

Since both peripheral nociceptors with endings in the skin and central nociceptors in the DRG and spinal cord become sensitized upon continuous activation, activation of NF-Kappa B is an important and critical stimulator of neuropathic sensitization.
2. Activation of Toll-Like Receptors by Microbes Activate Gene Transcription by NF-Kappa B That Sensitizes Activate Nociceptors Keratinocytes constitute about 90% of epidermal cells and have many receptors that that can cause nociceptor activation. Among the most important are Toll-Like Receptors (TLRs), molecules that recognize conserved molecular structures of bacteria, fungi and viruses. Upon activation, TLRs trigger multiple inflammatory and nociceptor activating pathways, all of which lead to NF-Kappa B activation.
3. Activation of NF-Kappa B Produces Chemokines that Attract Inflammatory Cells One of the most important consequences of NF-Kappa Bis to stimulate the production of chemokines, including IL-8, that attract and activate neutrophils, a blood-borne white blood cell (WBC) that typically constitutes over 50% of all WBCs in the blood. Neutrophils are the first responders to any type of trauma, infection or inflammatory process and accumulate at the triggering site in massive quantities. Upon activation by IL-8 and other inflammatory mediators, neutrophils produce massive levels of powerful oxidants, reactive oxygen species (ROS; e.g., superoxide, hydrogen peroxide, nitric oxide and hypochlorous acid) that rapidly deplete GSH from cells, including nociceptors, thus promoting oxidative activation of NF-Kappa Band activation of many kinases, including Protein Kinase A, Protein Kinase C and Mitogen-Activated Protein Kinases that act to amplify virtually all inflammatory pathways that directly activate nociceptors.

Activation of these multiple independent inflammatory pathways and inflammatory cells result in intense activation of nociceptors that contribute to the development of neuropathic sensitization and neuropathic pain and pruritus.

Such activation of nociceptors also causes them to release Substance P that directly triggers mast cell activation and release of histamine, TNF-alpha, IL-1, IL-6, IL-8 and many more inflammatory substances that further activate nociceptors. Due to the simultaneous activation of multiple inflammatory and nociceptor-activating pathways, there is a net amplification of nociceptor activation that is known to directly lead no neuropathic pain and pruritus.

4. Complexes of Strontium, and the Two Counterions, Cysteine-Based Anti-Oxidants and Polyhydroxyphenols, Block Nociceptor Activation by Blocking Multiple Inflammatory Pathways at Multiple Independent Steps in a Synergistic Fashion As described previously, by interfering with intracellular calcium dynamics within nociceptors, strontium in effect garbles the normal calcium-encoded signals that contain the pain and pruritic signals that ultimately produce the conscious appreciation of pain and pruritus. Strontium also binds to many critical calcium-dependent pathways that normally activate nociceptor pathways, including inflammation-triggering kinases that lead to NF-Kappa B activation and continued nociceptor activation.

The two counterions act at different steps in the same inflammatory pathways inhibited by strontium, and thus in effect amplify the basic anti-irritant activity and nociceptor-protective activities of strontium. Examples of the key strontium-amplifying activities of these two specific counterions are discussed below:

A. Cysteine-Based Anti-Oxidants Inhibit Multiple Strontium-Regulated Inflammatory Pathways that Activate Nociceptors Upon topical application of a cysteine-based anti-oxidant to the skin, the acetyl group of the cysteine-based antioxidant is rapidly removed leaving free cysteine Cysteine is the rate-limiting amino acid that controls the synthesis of reduced glutathione (GSH). Accordingly, administration of a cysteine-based anti-oxidant to skin rapidly increases the concentration of GSH and reduces the intracellular concentration of oxidized glutathione (GSSG), thus normalizing a nociceptor's redox state. This has the immediate effect of inhibiting the activation of NK-Kappa Band the activation of many other redox-sensitive inflammatory pathways, thus reducing nociceptor activation by both direct and indirect pathways. Cysteine-based antioxidants also have a unique anti-oxidant activity due to their thiol (SH groups) that suppress the ability of nitric oxide to covalently bond to and activate inflammatory kinases that are known to directly contribute to neuropathic conditions. Cysteine-based anti-oxidants also directly inactivate other oxidants that activate inflammatory pathways and, most importantly, they inhibit nociceptor activation. By combining a cysteine-based anti-oxidant with strontium, one of the most important regulatory controls of nociceptor activation is reduced by shifting the nociceptor's redox state to a high GSH/GSSG ratio.

Due to its thiol group, cysteine-based anti-oxidants also have the ability to directly bind to the thiol groups of cysteine residues within molecules that are part of inflammatory pathways that contribute to nociceptor activation. Since there are many thiol-sensitive regulatory molecules, cysteine-based anti-oxidants have the ability to block oxidation of critical cysteines in such molecules and thus block activation that leads to increased inflammation and nociceptor activation. For many redox sensitive cysteine regulated pathways, the concentration of calcium within nociceptors is increased and, as for many other nociceptor activators, the resultant calcium-concentration encoded pain, pruritus and activation signals contribute to the formation and the long-term continuation of neuropathic conditions. By blocking such cysteine oxidation induced calcium release, cysteine-based anti-oxidants contribute to strontium's inherent ability to similarly inhibit calcium-encoded signals, but by non-strontium mechanisms. By blocking calcium-dependent signals with distinct mechanisms, the overall nociceptor inhibitory activity is increased.

B. Polyhydroxyphenols Inhibit Multiple Strontium-Regulated Inflammatory Pathways that Activate Nociceptors Like the cysteine-based anti-oxidant, the polyhydroxyphenols are powerful antioxidants. The polyhydroxyphenols, however, possess several unique anti-oxidant mechanisms not possessed by the cysteine-based anti-oxidant. The polyhydroxyphenols act to inhibit multiple oxidant-generating pathways that are only indirectly affected by cysteine-based anti-oxidants. By combining multiple, independent anti-oxidant inhibitory mechanisms, the counterions in combination act with a maximum anti-potency to inhibit redox sensitive activation of NF-Kappa B and many other nociceptor activation pathways that are triggered by exposure to oxidants.

An exemplary polyhydroxyphenol in the practice of the present disclosure is gallic acid (3,4,5-trihydroxybenzoic acid). Gallic acid (GA), and similarly structured polyhydroxyphenols, have multiple anti-inflammatory, anti-oxidant and inflammatory cell inhibitory activities that amplify the strontium regulated pathways that lead to suppression of nociceptor activation.

The polyhydroxyphenolic structure of gallic acid, caffeic acid, quercetin, luteolin, myricetin and similar polyhydroxyphenolic anti-oxidants provide such molecules with a number of important properties that both inhibit nociceptor-activating pathways suppressed by strontium and provide specific abilities to bind to and suppress several important kinases that are known to be important for development of neuropathic pain and pruritus conditions.

These molecules all have hydroxyl groups that are, in one embodiment, adjacent to each other on the phenolic moiety in meta and para positions and mimic the three dimensional structure of adenosine triphosphate (ATP), a molecule that must bind to the active sites of kinases like protein kinase C and other regulator kinases that are part of signal transduction pathways that active multiple inflammatory pathways, activate NF-Kappa Band directly activate nociceptors. These kinases are also known to be necessary for development of neuropathic nociceptor sensitization and neuropathic pain and pruritus.

Polyhydroxyphenols also directly bind to components of NF-Kappa Band cause a direct inhibition of activation. The ability of the counterions to inhibit NF-Kappa B activation by multiple independent mechanisms produce an inhibitory effect greater than inhibition by only one mechanism.

The polyhydroxyphenols also inhibit the expression of multiple cellular adhesion molecules like ICAM-1, VCAM-1 and members of the selectin adhesion molecules that enable neutrophils and monocytes to extravasate from blood vessels and accumulate at sites of inflammation, thus contributing to nociceptor activation.

Polyhydroxyphenols also have multiple anti-oxidant activities that have mechanisms distinct from those of the cysteine-based anti-oxidants. For example, gallic acid and the other polyhydroxyphenols directly inactivate supereoxide, hydrogen peroxide, hydroxyl radicals and hypochlorous acid, thus preventing them from shifting the intracellular GSH concentration from being reduced, which activates NF-Kappa Band other redox activated inflammatory regulatory molecules and molecules that directly activate nociceptors.

The polyhydroxyphenols also possess a unique ability to inhibit the Fenton Reaction by which low concentrations of ferrous iron (Fe2++) and copper (Cu++) catalytically produce the highly toxic and inflammatory hydroxyl radical that is a powerful inflammation activator.

In one embodiment, the polyhydroxyphenol is selected from the group consisting of: gallic acid, quercetin, caffeic acid, myricetin, and leutolin. Such molecules have powerful inhibitory activities on one of the most important inflammatory molecules present in the skin, the mast cell. Mast cells are present in the dermis and submucosal tissues throughout the body and are among the most important sources of preformed inflammatory mediators like histamine, TNF-alpha, IL-1, IL-6.

IL-8 and over 20 other chemokines and inflammatory mediators, all of which directly or indirectly activate nociceptors. Nociceptor activation is also a major stimulator of Substance P release from Type C Nociceptors that directly activate mast cells, neutrophils and every other type of inflammatory white blood cell. The combined ability of strontium to inhibit nociceptor activation, Substance P release and polyhydroxyphenolic inhibition of mast cell activation provides a powerful additive synergistic inhibitory activity on inflammation and nociceptor activation.

Both cysteine-based anti-oxidants and polyhydroxyphenols additionally are powerful inhibitors of prostaglandins and leukotrienes, particularly PGE2 and LTB4. PGE2 is one of the most important nociceptor sensitizers that is synthesized in virtually all inflammatory conditions. LTB4 is one of the most important attractants and activators of neutrophils that are the first cell to accumulate in large numbers at sites of trauma, irritation, infection and inflammation and are among the most important triggers of nociceptor activation. Each class of counterion inhibits prostaglandin and leukotriene synthesis by different mechanisms.

Both counterions also have a critical ability to inhibit several inflammatory and nociceptor activating pathways that are stimulated by strontium, thus potentially enhancing strontium's ability to inhibit acute and chronic pain and pruritus and to inhibit nociceptor sensitization that is known to be important for development of neuropathic conditions.

In particular, strontium's ability to activate the Calcium-Sensitive Receptor (CaSR) on cells, including nociceptors is known to activate Protein Kinase A, Protein Kinase C and NF-Kappa B. Activation of each of these molecules is known to contribute to nociceptor activation and neuropathy development. The counterions limit such activation. Indeed, the combination of the cysteine-based anti-oxidant polyhydroxyphenols inhibit the activation of each of these strontium activated molecules by multiple independent mechanisms, thus negating the undesirable activities of strontium that otherwise limits it's overall anti-irritant activity and ability to inhibit the development and maintenance of neuropathic conditions.

By combining strontium with the counterions described herein, the resultant complexes are more efficient inhibitors of many of the same nociceptor-activating pathways that are inhibited by strontium by multiple, overlapping and distinct mechanisms. Finally, the combination these strontium amplifying molecules also inhibit strontium-activated pathways that contribute to pain, pruritus and development of neuropathic diseases.

Also contemplated is a composition that incorporates a combination of strontium with a mixture of polyhydroxyphenols. Using more than one polyhydroxyphenol has a synergistic effect due to the differential activities of each polyhydroxyphenol. It is contemplated that this synergistic effect has enhanced efficacy in treating sensory irritation that includes but is not limited to pain, pruritus, and development of neuropathic diseases. In one embodiment, the mixture includes monophenolic and polyphenolic polyhydroxyphenols. In one embodiment, the mixture includes monophenolic and biphenolic polyhydroxyphenols. In another embodiment, the mixture includes monophenolic and triphenolic polyhydroxyphenols. In another embodiment, the mixture includes biphenolic and triphenolic polyhydroxyphenols. In another embodiment, the mixture includes monophenolic, biphenolic, and triphenolic polyhydroxyphenols. In another embodiment, the mixture includes an ATP analogue with a monophenolic, biphenolic, or triphenolic polyhydroxyphenol. In yet another embodiment the mixture of polyhydroxyphenols is gallic acid and caffeic acid. In another embodiment, the mixture of polyhydroxyphenols is myricetin and caffeic acid. In another embodiment, the mixture of polyhydroxyphenols is myricetin and gallic acid. In another embodiment, the mixture of polyhydroxyphenols is myricetin, gallic acid, and caffeic acid.

The Complexes of the Present Disclosure

The compositions and formulas of the present disclosure have two general design & therapeutic goals: (1) Reduce the Negative Effects of Strontium on Neuropathic Treatment; and (2) Increase Strontium's Beneficial Activities for Neuropathy Treatment.

After strontium was first commercialized, it became clear that while strontium was safe and effective in many commercial applications, it suffered from a number of deficiencies that ultimately limited its potential therapeutic utility. For example, strontium at a concentration of 2-6% in a formulation frequently caused transient stinging if the treated skin was broken or had a damaged 'barrier' due to trauma, chemical exposure, infection or disease. Patients with 'diaper rash', both infants and people who are incontinent usually experienced intense pain described as stinging for 5-10 seconds when using a 4 or 6% strontium formulation. While not harmful, it was not tolerable for many infants Similarly, strontium at higher concentrations was not be applied to thermal burns, cuts or skin that had been highly excoriated due to scratching. Attempts to develop emulsion-based lotions or creams were limited by the inherent emulsion destabilizing effect of electrolytes like strontium and its counter ions that disrupt the very electrostatic forces that create emulsions.

In one embodiment, the compositions of the present disclosure are tripartite complexes containing at least three components, of which, one component is strontium. In another embodiment, the compositions of the present disclosure are bipartite complexes containing at least two components, of which, one component is strontium. The components of the tripartite and bipartite complexes are discussed below.

A. Strontium

Strontium is present as a divalent cation. Strontium is designated by its commonly used atomic symbol, 'Sr' and is depicted below.

Strontium mimics the ability of calcium to pass through voltage dependent calcium channels. As such, it may compete with Ca++ for binding to some receptors. Calcium is thought to play a role in the pain process by regulating the release of neurotransmitters, and thus strontium's analgesic effect may be in preventing calcium's binding to nerve cells.

Strontium is available as an inorganic or organic salt which is water soluble at room temperature in the range of 1 to 100 g/l. Inorganic salts include, for example, strontium chloride, strontium sulfate, strontium carbonate, strontium nitrate, strontium hydroxide, strontium hydrosulfide, strontium oxide, strontium acetate, etc. Organic salts include, for example, negatively charged organic acid such as a mono-, di-, tri- or quatro-carboxylic acid, or an amino carboxylic acid that may have a linear or branched carbon chain of from 2 to 30 carbon atoms and one or more amino groups attached thereto. The amino carboxylic acid may be a natural or synthetic amino acid. Examples of organic strontium salts include, for example strontium glutamate, strontium aspartate, strontium malonate, strontium maleate, strontium citrate, strontium threonate, strontium lactate, strontium pyruvate, strontium ascorbate, strontium alpha-ketoglutarate or strontium succinate. Other examples of strontium salts, and methods for preparation thereof, can be found, for example, in US Published Application No. 2010/0048697.

In the form of an organic salt, it should be understood that the counterion cannot have a higher affinity for strontium than the anti-oxidants and/or polyhydroxyphenols described herein for forming strontium complexes.

B. Polyhydroxyphenols

Polyhydroxyphenols are phenolic compounds possessing at least two hydroxyl groups, preferably in the ortho and para positions. One exemplary compound is 3,4,5-trihydroxy benzoic acid, also called gallic acid. The term "polyhydroxyphenol" does not include carboxylic acids, such as ranelate.

The polyhydroxyphenol can be added to the compositions described herein in essentially purified form, or they can be added in the form of polyhydroxyphenol containing plant extracts, such as green tea and soy extracts.

The flavonoids are polyphenolic compounds possessing 15 carbon atoms; two six-carbon benzyl rings that are usually joined together by a linear, saturated three carbon chain. Other flavinoids may consist of two benzyl rings joined together by a third 5- or 6-carbon ring structure. Flavinoids constitute one of the most characteristic classes of compounds in higher plants. Many flavinoids are easily recognized as the pigments in flowering plants.

The polyhydroxyphenol may also function as an antioxidant. For example, gallic acid is a tri-hydroxyphenolic structure that has anti-oxidant activity. The monomeric phenolic compounds include for example, gallic acid (3,4, 5-trihydroxybenzoic acid) and caffeic acid. Both compounds have a carboxylic acid group, which may be esterfied with a sugar moiety such as glucose. In the case of gallic acid, such esterfication produces glucogallin. Other organic esters may also be effective, such as the ethyl ester of gallic acid, ethyl gallate, or the propyl ester of gallic acid, propyl gallate.

Also contemplated by the present disclosure are polymeric phenolic compounds that have two or more aromatic rings that typically, but do not necessarily have the same structure. One such example is reservatrol. Another is pentagalloyl glucose, which consists of five gallic acid residues that are esterfied to one glucose molecule. This molecule will be cleaved in vivo by non-specific esterases, which free the individual gallic acid residues. The use of such forms of polyhydroxyphenolic compounds has the added advantage of lowering osmotic activity, since one molecule of pentagalloyl glucose produces one unit of osmotic activity, as compared to five units of osmotic activity produced by the use of five separate molecules of gallic acid.

Tannic acid is another example of a high molecular weight gallic acid polymer in which one or more esterfied gallic acid residues are esterfied to a central glucose molecule.

Ellagic acid is an example of a gallic acid dimmer. While this molecule no longer possesses the gallic acid-like phenolic structure, it does maintain many of the same bioactivities of gallic acid and is thus useful in the practice of the present disclosure.

Compounds having a flavone backbone include, for example, quercetin, and epicatechin (EC) and derivatives thereof, such as epigallocatechin gallate (EGCG found in green tea), epigallocatechin (EGC) and epicatechin gallate (ECG).

Other polyhydroxyphenolic compounds include, for example, myricetin, luteolin, naringen, genistein and nordihydroguaiaretic acid (NDGA).

In one particular embodiment, the polyhydroxyphenols that are useful also exhibit one or more carboxyl groups, such as gallic acid and caffeic acid. The carboxyl group can serve as an additional counterion, and also assist in matrix formation with an optional polyanionic polymer.

In another embodiment, the polyhydroxyphenols that are useful in the practice of the present disclosure are inhibitors of Protein Kinase C (PKC) isozymes, and in particular, PKC epsilon. This is particularly true of strontium-polyhydroxyphenol complexes, since the strontium can mimic the effects of calcium as a cofactor for PKC. For example, luteolin and quercitin are known to inhibit PKC isozymes. See, for example, Cancer Res. 70(6): 2415-2423 (2010); and Biochem. Pharmacol. 38: 1627-1634 (1989). Also as described in demonstrated by both of these articles, methods for determining the degree of inhibition of PKC by compounds are known in the pharmaceutical arts. As used herein, the polyhydroxyphenol will be considered to be a PKC inhibitor if it suppresses 10% or more of the activity of the PKC.

In yet another embodiment, the polyhydroxyphenols and their corresponding strontium complexes are known inhibitors of calmodulin. More particularly, they inhibit calmodulin-promoted phosphodiesterase activity. See, for example, Plant and Cell Physiol. 26(1) 201-209 (1985), which describes inhibition of calmodulin-promoted phosphodiesterase activity by flavonoids such as catechin, epicatechin, quercetin, caffeic acid and naringenin. As used herein the polyhydroxyphenol will be considered to be a calmodulin inhibitor if it suppresses 10% or more of the activity of calmodulin.

In still another embodiment, the polyhydroxyphenols and their corresponding strontium complexes are known ATP analogues. This is the mechanism by which they inhibit protein kinases in that they compete with ATP for the protein kinase ATP binding site, which prevents protein kinase from being active. Studies of the activities of various ATP analogues, such as flavonoids, are known in the literature. See, for example, Phytochemistry Reviews 1:325-332 (2002), wherein the effect of flavonols on ATP-dependent activities was studies.

C. Cysteine-Based Compound

Cysteine is abbreviated by the three letter amino acid code, Cys. In chemistry, a thiol group contains sulfur that is covalently bound to two groups, (1) a carbon, designated 'C', or if the carbon is part of a longer chain of carbon atoms, the letter 'R' is frequently used to designate this carbon chain. (2) Attached to the carbon atom by a covalent bond is the second part of a thiol group, a hydrogen atom, designated by its atomic symbol, 'H'. The intact thiol group is thus designated '—SH' in which the SH group is bound to a carbon, and is commonly designated '—C—SH', or if the —SH thiol group is attached to a chain of carbon atoms, R—SH is the commonly used representation. Thiols are also referred to as mercaptans in reference to their ability to bind strongly to the element mercury—thus the Latin term 'mercurium captans' that literally means 'capturing mercury'.

The term "cysteine-based compound" includes cysteine and cystine. Alternatively the cysteine-based compound is acetylated at the amino group of the cysteine to produce N-acetyl-cysteine, commonly abbreviated acetylcysteine or NAC. Cysteine exists in two enantiomeric forms, designated 'L-cysteine' and 'D-cysteine', of which the L form is used in living organisms while the D form is not. While both the L and D forms are contemplated in the present disclosure, the L form of acetylcysteine is most preferred, i.e., NAC. If the D form of NAC is intended, it will be referred to as D-NAC. In addition, both L-Cys and D-Cys can form disulfide bonds between the two thiol groups to form a 'dimer', literally a pair of Cys molecules. Such disulfide bonds occur in many proteins and play a critical regulatory role in biochemical pathways due to the ease of their reversible formation by oxidative processes and dissolution by reductive processes. By convention, a disulfide-bonded dimer of cysteine is termed cystine. Thus one cysteine molecule under appropriate reducing conditions or enzymatic processing will yield two cysteine molecules. Cystine can be formed from either two L-Cys molecules, two D-Cys molecules, or one L-Cys and one D-Cys molecules. Another exemplary cysteine-based compound is N,S-diacetylcysteine. All of such variants are incorporated within the present disclosure.

D. Aromatic Amino Acids

Aromatic amino acids have an aromatic ring in their side chain. The aromatic amino acids are phenylalanine, tyrosine, tryptophan and histidine. All amino acids, except glycine, have two isomers which are chiral and are referred to as "D" and "L." The L form is the predominant form in living organisms and is the form used to build proteins. While both D and L forms of the aromatic amino acids are contemplated in the present disclosure, the L form is preferred.

Aromatic amino acids act as agents that increase the receptor response to strontium and calcium. The site which the aromatic amino acid binds differs from the strontium and calcium binding site.

E. Cleavable Bonds

In one embodiment, the complexes of the present disclosure utilize a cleavable bond to join the polyhydroxyphenol and the cysteine-based compound together in the tripartite complexes. Complexes which use a cleavable bond to join the polyhydroxyphenol and cysteine-based compound together in the tripartite complexes will be referred to as the "conjugated" form of the compounds.

As defined above, a cleavable bond is a chemical bond joining two molecules together that can later be broken, thus releasing the two molecules from each other. The present disclosure contemplates using cleavable bonds that are known in the art, examples of which include, but are not limited to peptide bonds, thioesters bonds, enzymatically cleavable bonds, disulfide bonds, pH dependent bonds, and other covalent bonds.

The use of cleavable bonds in the present disclosure may create a less active form of the compound that can be converted to an active form. The benefits of using a less active form are known in the art. For example, the less active form may be used to enhance the stability of a compound allowing for an increase the shelf-life or a greater range of storage temperatures. The less active form may also be used to ensure that the compound reaches it target destination before becoming active.

The use of cleavable bonds in the present disclosure offer other advantages that may improve the performance of the complex. For example, the conjugated form may be used to reduce the osmolarity of a chemical compound, which in the present disclosure is useful since the human body has molecular sensors that recognize changes in osmolarity and trigger pain and itch pathways. The conjugated form may also be used to change the solubility of a compound, for example, making the compound more lipophilic to allow better uptake into cells.

As described elsewhere herein, limiting the osmolarity of the present composition herein may be beneficial. Accordingly, conjugating polyhydroxyphenol to the cysteine-based antioxidant lowers the osmolarity by approximately one third, thus enhancing efficacy. The addition of a neutral or anionic polymer reduces the osmolarity even further by allowing multiple tripartite complexes to attach to one polymer.

In one embodiment, the cleavable bond of the conjugated form of the compound is cleaved upon application of the compound to the skin. One example of this embodiment is the use of thioester to join gallic acid to NAC. When this compound is applied to human skin, non-specific esterases on the surface of the skin cells cleave the thioester bond.

In another embodiment, only a small percentage of the cleavable bonds of the conjugated form of the compound are cleaved upon application of the compound to the skin or thereafter, the majority of the conjugated form of the compound is taken into the cell where the cleavable bonds are cleaved. The uptake of the conjugated form of the compound allows for a greater concentration of strontium to be present within a cell than applying a strontium salt to the skin or orally ingesting strontium.

In another embodiment, the cleavable bond is cleaved upon application of a second compound containing a cleaving agent. A cleaving agent is an agent that cleaves specific chemical bonds. The second compound can be applied to the skin immediately after the application of the conjugated form of the compound or alternatively, the two compounds can be mixed together immediately before application to the skin. Examples of cleaving agents include, but are not limited to enzymes, reducing agents, oxidizing agents, light, and chemicals that induce pH changes.

In one embodiment, the complexes of the present disclosure include: 1) one atom of strontium; 2) one molecule of gallic acid; 3) one molecule of N-Acetyl-L-Cysteine, (NAC). In another embodiment, the gallic acid and NAC are joined by a thioester and complexed with gallic acid.

Optional Ingredients

1. Optional Neutral or Ionic Polymers

A. Hyperosmotic Formulation Instability of Strontium Formulations

Strontium's anti-irritant activity is due to the divalent strontium ion. Due to its dual positive charges, anionic counterions are required to balance the electrostatic charge and thereby create a strontium salt. Among many possible strontium salts, preferred salts included strontium nitrate a d strontium chloride, either as the hexahydrate or in an anhydrous salt form. In both of these salts, the negatively-charged counterions, Nitrate (N03-) or Chloride (Cr) contribute to the ionic strength and osmolarity of the formulation, but not to the overall anti-irritant benefits. Since many formulations such as lotions, creams and hydrogels rely on a delicate balance of factors that produce stable emulsions or hydro gels, formulations with high ionic strengths commonly prevent stable emulsion formation. For example, emulsions in which more than about 6-7% strontium nitrate or strontium chloride hexahydrate, (equivalent to about 2% elemental strontium) are incorporated tend to be unstable and separate. Similarly, hydrogels containing more than about 12% to 13% (equivalent to about 4% elemental strontium) of these salts also tends to be unstable. Clinical studies have shown that higher strontium concentrations produce increased clinical benefits. Consequently, it is medically and commercially advantageous to create commercially acceptable and stable formulations with high strontium concentrations. Since two thirds of the strontium nitrate or chloride salt represents ions that act to destabilize formulations, it is impossible to achieve this goal using available ingredients.

B. Hyperosmotic Formulations Can Also Physically Damage Tissues and Cause Pain Topical formulations with high osmotic activity (over 400 mOsm, such as between 400 and 2000 mOsm) may also damage delicate tissues and may cause pain, especially in non-keratinized skin that have a mucous membrane or that has a damaged 'barrier function' due to physical trauma, infection or inflammation. Such hyperosmotic-induced damage is popularly known as ' . . . the salt in the wound effect . . . ' and it occurs when osmotic forces cause water to flow out of the cells and tissues into the hyperosmotic formulations. Recent scientific reports also demonstrate that application of hyperosmotic formulations can directly activate certain molecules that act as osmolarity sensors and, when activated, activate pain sensing nerves and immune and non-immune cells that can produce inflammation and cellular damage. This recent understanding has potentially critical importance for the goal of preventing the development of chronic or neuropathic pain.

The potential importance of this observation has critical importance for the treatment of or the prevention of neuropathic pain development since chronic nociceptor activation is known to be required for painful neuropathic conditions to develop. The recent discovery that there are multiple ion channels and related hyperosmotic molecular sensors that trigger nociceptor activation upon exposure to hyperosmotic topical formulations suggests that their chronic use may predispose the development of neuropathic pain conditions if there is coexisting chronic or severe damage to nociceptors. In this scenario, long-term application of a hyperosmotic formulation to skin, and especially to delicate mucous membranes of, for example, the vaginal or cervical mucosa my cause low level, but long-term activation of nociceptors, thus contributing to their sensitization. It is believed that progression of from an acute, transient pain state to a chronic, long-lasting, 'neuropathic state' is due to continued excessive nociceptor activation that results in increased expression of genes that reduce the magnitude of an irritant stimuli, also called the irritant or nociceptor activation 'threshold' and thus cause increased nociceptor activation and an increased perception of pain and/or pruritus. Additionally, these genes can also increase the synthesis of inflammation-producing molecules that further irritate the nociceptors, thus producing what is commonly termed 'a vicious spiral' of increasing sensory irritation and inflammation.

C. Hyperosmotic Formulations Can Also Increase Infection by Herpes & HIV

In addition to causing painful or pruritic sensations and inflammation, even low-level, but chronic exposure to nociceptor-activating irritants can predispose to infection by a multitude of pathogenic microbes of which Herpes simplex viruses 1 and 2 (HSV) and the Human Immunodeficiency Virus (HIV) cause the greatest threat to public health. While a detailed explanation of the many and varied reasons for why nociceptor activation and coexisting inflammation facilitates infection by HSV and HIV is not discussed in detail herein, in essence, the release by Type C Nociceptors of inflammatory neuropeptides like substance P is known to damage the anatomical 'barriers' of both keratinized skin and mucosal membranes that block viral infection. The resultant inflammation is also known to activate inflammatory immune cells that, ironically, contribute to the ability of both HSV and HIV to cause acute infection and in the case of HSV, reactivation of an existing latent infection.

Application of hyperosmotic topical formulations of, for example, lubricants or microbicides, to the mucous membranes of male or female genitals or to the vaginal, cervical or anal tissues may greatly increase the possibility of transferring one of these viruses or other pathogenic microbes that cause sexually-transmitted diseases from an infected person to an otherwise healthy person. It is therefore be advantageous to create strontium containing formulations with high strontium concentrations that are designed to minimize the osmolarity of the formulation. It is one object of the present disclosure that is inherent in its molecular design to provide a strontium-containing molecule having a minimal osmotic activity and that possesses multiple therapeutic components that maximize the amount of therapeutically beneficial strontium that can be applied.

In one embodiment, the compositions of the present disclosure include a strontium complex and a polymer capable of ionic association with the complex, in which case the complex and the polymer form a matrix. Such matrix formation enhances the bioavailability of the complexes and therefore prolongs the therapeutic effect of such complexes. In particular, when the strontium complex includes a polyhydroxyphenol, such compounds have a high affinity for polymers, such as polyvinylpyrrolidone (PVP).

For example, PVP is commonly used as an inert carrier of therapeutically active molecules. Due to the varying polar structure of the PVP polymer, it presents multiple, repeating sites to which atoms and molecules may bind via ionic forces. Upon subsequent exposure to ionic media, such as water, the bound substance may be released into the media over an extended period of time. Thus facilitating gradual release of the substance as a function of pH and other adjustable conditions, such as temperature, etc. As such, the PVP acts as a "molecular reservoir" providing for sustained release of therapeutic substances.

The PVP polymer may be in its native form, or it may be chemically modified by derivatization and/or crosslinking to adjust the "releasing" properties of the polymer.

The polyhydroxylated phenols, such as gallic acid, have a high affinity for PVP. As such, the combination of PVP, gallic acid and divalent cationic strontium forms a complex ionic matrix that facilitates controlled release of the strontium after administration.

Such polymer-based compositions also minimize osmolarity which can lead to unstable formulations and physically damage tissues and cause pain. For example, topical formulations with high osmotic activity may damage delicate tissues, especially in nonkeratinized skin that has a mucous membrane or a damaged "barrier function" due to physical trauma, infection or inflammation.

Neutral or anionic polymers include, for example, polyvinylpyrrolidone (PVP), cyclodextrins, carragenans, alginic acid, xanthan gum, sulfated polysaccharides such as carrageenan, dextran sulfate, pentosan polysulfate, condroitin sulfate, heparin sulfate, etc.

Matrices formed between monomeric compounds such as flavonoids and polymers such as cyclodextrin are known in the art. See, for example, PLoS ONE 6(4): e18033 (2011).

Formulation and Administration

There are two principle physical methods by which the elements that make up the complexes of the present disclosure can be administered to a patient.

Method 1:

In the first method, the strontium, and the counterions, a cysteine-based anti-oxidant, polyhydroxyphenol, or an aromatic amino acid form a single complex in which each the three atomic and molecular elements are held together by ionic chemical bonds. Such bonds are formed due to the two positive charges of the strontium cation and due to the negative charges present on the counterions that occur at physiological pH and lower. The three ionically bonded molecules form a "salt."

In one embodiment, the salt is formed by combining strontium with a cysteine-based anti-oxidant and a polyhydroxyphenol. In another embodiment, the salt is formed by combining strontium and two polyhydroxyphenols. In yet another embodiment, the salt if formed by combining strontium and two aromatic amino acids.

In one embodiment, the tripartate nature of the complexes of the present disclosure is represented by gallic acid having a negative charge, the divalent strontium atom possessing two positive charges, and N-Acetyl-L-Cysteine (Acetylcysteine, NAC) with its negatively charged carboxyl group. Due to the single negative electrostatic fields that surround the negatively charged carboxyl groups of both gallic acid and NAC, and due to their attraction to the two positive charges of the single strontium ion, these three substituents form a "salt".

In one embodiment, the counterions, a cysteine-based anti-oxidant and a polyhydroxyphenol, are conjugated together with a cleavable bond. The conjugated counterions are then combined with the strontium. The cleavable bond may be any type of cleavable bond known in the art that does not interfere with the ionic chemical bonds that will form between the strontium cation and the counterions. One non-limiting example is joining gallic acid and NAC together with a thioester bond.

Method 2:

The second method by which a complex of the present disclosure can be formulated and therapeutically administered to an animal or human subject is by the incorporation of the separate substituents in a pharmaceutically-acceptable vehicle or delivery system. For tripartite complexes, one atom of strontium, one molecule of a cysteine based anti-oxidant and one molecule of a polyhydroxyphenol are all added to a pharmaceutically-acceptable vehicle. For bipartite complexes, one atom of strontium and two molecules of polyhydroxyphenol are all added to a pharmaceutically-acceptable vehicle. Alternatively, for bipartite complexes, one atom of strontium and two molecules of aromatic amino acids are all added to a pharmaceutically-acceptable vehicle. This type of relationship in which a single atom or molecule is combined with other atoms or molecules on a one-to-one basis, that is in which an integer number of atoms or molecules are combined is referred to as on the basis of their molar relationships. In the example of the tripartite complex described above, the molar ratio of each substituent is 1:1:1, that indicates 1 atom of strontium+1 molecule of gallic acid+1 molecule of NAC. In the example of the bipartite complex, the molar ration of each substituent is 1:2, that indicates 1 atom of strontium+2 molecules of polyhydroxyphenol or aromatic amino acid.

In another embodiment, the pharmaceutically-acceptable vehicle to which the bipartite are tripartite complexes are added also contains a polymer. Due to the nature of the polymer, the ratio of strontium to counterion does not need to be one molecule of strontium to two molecules of counterions. The polymer itself provides multiple counterions to which the strontium ionically binds.

For certain therapeutic applications, it may be desirable to substitute a 'D' version of cysteine for L-cysteine that occurs within living organisms. For example, since L-Cys is used as a substrate for the synthesis of the tripeptide, glutathione, gamma-Glu-Cys-Gly, where Glu is the common three letter amino acid code for glutamic acid and Gly is the code glycine. Since the amount of cysteine that is available to a cell is the principle rate-limiting factor that determines how much glutathione is produced by a cell, increasing or decreasing the amount of cysteine can regulate intracellular glutathione synthesis. When NAC is administered to cells, either topically or systemically, the acetyl group is rapidly removed within a cell and the cysteine is used to create new glutathione.

Glutathione is known to be the most abundant and important intracellular thiol anti-oxidant present in all cells, and since the amount of glutathione in cells is known to be a powerful regulator of cellular activity, function and activation of genes that produce powerful inflammatory molecules, including pro-inflammatory cytokines. For this reason, it may be therapeutically advantageous for certain conditions or diseases to deliver one strontium atom in combination with two L-Cysteine molecules, or one strontium atom in combination with one L-Cystine molecule, that will be reduced to two L-cysteine molecules within cells) that will result in the maximum synthesis of glutathione within cells.

For treating other conditions or diseases, it may be advantageous to deliver an intermediate amount of L-cysteine for conversion into glutathione. Since D-cysteine is not used to create glutathione, but it does retain its direct anti-oxidant activity due to its thiol (—SH) group, it is certainly useful in the practice of the present disclosure, wherein the D-Cys delivers a maximum level of direct thiol-related anti-oxidant activity while delivering only an intermediate level of new glutathione synthesis.

The present disclosure contemplates the use of such variants of the complexes since a particular variant may have therapeutic advantages when treating certain types of conditions or diseases. For example, for the treatment of neuropathic pain or neuropathy pruritus in HIV-infected patients, it is well known that the intracellular concentration of glutathione, the principle intracellular thiol anti-oxidant may be drastically reduced to a point that further harm is caused to the patient. Such glutathione depletion is believed to exacerbate many of the inflammatory pathways that contribute to the potentially intense pruritus and burning pain that accompanies HIV infection and HIV therapy. Since administration of either cysteine or, especially NAC is known to greatly increase intracellular glutathione, treatment of HIV-induced neuropathy is one of many examples in which it may be therapeutically preferable to use a complex variant with more than one functional cysteine group.

The compositions of the present disclosure are useful in treating pain, pruritis, inflammation and irritation. For example, they are useful for the following: 1) treating keratinized skin due to: acute sensory irritation (caused by allergies, insect bites venomous pain, etc.); delayed reactions (caused by poison ivy, nickel allergy, diseases such as atopic dermatitis, psoriasis); ionizing radiation (caused by sunburn, therapeutic xrays); and chemically induced irritants (such as cleaning supplies, depilatory treatments, gasoline.) and 2) treating neuropathic pain such as post-herpetic neuralgia, shingles, nerve damage, nerve oversensitization, stump pain, diabetic neuropathy, etc.

Other examples of conditions in which the present compositions are useful include, for example, herpes, HIV, itching, inflammation, irritation of the eyes, contraceptive irritation, thermal bums, skin damage, oral irritation, radiation, chemical bums, wounds, diabetic ulcers, etc.

EXAMPLES

The examples that follow demonstrate the ability of a combination of strontium, a polyhydroxyphenol and a cysteine-based anti-oxidant to treat pain and pruritus caused by a variety of conditions, some that occur in response to an acute injury or stimulus, others that have chronic and/or neuropathic origins. As previously described, the pain or pruritus-transmitting nociceptors that are suppressed by these compositions occur throughout the body and their most peripheral endings line the outmost viable surfaces of keratinized skin and epithelial surfaces covered by mucous membranes in the eye, the mouth, throat, esophagus and gastrointestinal tract, the respiratory and genitourinary tracts.

Example 1 below describes the use of the complexes described herein to treat pain in the mouth is a particularly important indicator that such compositions will be an effective pain treatment for many other painful oral conditions including oral and throat ulcers due to infection, trauma, chemical irritant exposure, malignancy, for example, and pain that occurs in the throat (a 'sore throat'), aphthous ulcers and infections that occur in and around the nociceptors themselves as in Herpes simplex infections.

In all these conditions, there are many different conditions and stimuli that activate Type C nociceptors nociceptors. No matter what proximal stimulus causes TCN activation, there are only two responses that can occur, a painful sensation most often described as burning, stinging or tingling, itching or on occasion both of these sensations. As Examples 1 and 2 below demonstrate, the complexes of the present disclosure are highly effective at suppressing the pain caused by physical trauma to the oral cavity, the mucosa, teeth, bone and surrounding structures due to cracked teeth, and from subsequent extraction of two adjacent molars that caused severe physical trauma from subsequent surgical excision of gum mucosa, tooth extraction and excision of the tooth root adherent to the bone of the tooth socket and sewing of the, and trauma and destruction of the pain-sensing nerves that innervate tooth pulp, as well as pain sensing nerves in the adjacent bone and soft tissues.

The extraction of these molars and accompanying surgical procedures resulted in activation of not only nociceptors in the teeth, gums, mucosa and bone, but as occurs in all trauma and inflammation, neutrophils were rapidly attracted to the site of bleeding and trauma and were activated to prevent normal bacterial flora from causing infection of the surgical site. In such a surgical procedure with accompanying physical trauma, most if not all of innate and adaptive immune and inflammatory pathways that are known to trigger pain were strongly activated. The fact that a topical treatment with the complexes of the present disclosure produced such rapid and complete pain relief strongly suggests that it will also be an effective pain reliever in many other painful conditions in the oropharynx, and in pain produced by trauma or other inflammation-inducing processes in other portions of the body. It is important to note that the presence or absence of a keratinized layer of cells on the tissue that is being treated has no bearing or influence on the ability of the complexes of the present disclosure to effectively treat pain, pruritun or related nociceptive sensations. The fact that nociceptors in general and Type C Nocieptors in particular have essentially the same functions, properties and abilities to transduce danger signals into calcium-encoded pain and pruritic sensations suggests that such nerves will have similar, if not essentially identical responsiveness to the therapeutic effects of the complexes of the present disclosure. While the presence or absence of a keratinized layer of cells will influence the rate and degree of penetration of a topically-applied treatment like the complex of the present disclosure, it will not appreciably affect the ability of the complex to suppress pain, pruritus or other nociceptive sensations or neurogenic inflammatory reactions.

As demonstrated by the examples herein, the complexes of the present disclosure are especially effective at suppressing the pain that occurs in response to physical manipulation or trauma to the teeth, and the tooth-bone interactions that result in the strong adherence of teeth to their bony sockets. Such trauma occurs especially in tooth manipulations such as orthodontic procedures, especially those involving braces or other physical wires, attachments or devices that have as a therapeutic goal straightening or otherwise aligning or moving teeth. Pain from physical trauma to the face, skull, mouth and oropharynx from accidents, surgery or disease will also be particularly responsive to the pain-reducing benefits of the complexes taught herein.

Example 1—Oral Delivery

A 59 year old male experienced two cracked molars (lower left rear-most and adjacent) that required two temporary crowns to be installed prior. Neither crowns were completely liquid tight and liquids ingested penetrated under the crown and directly contact the exposed tooth pulp nerves in both molars.

Within about a minute eating dill pickles one day after the crowns were installed, the subject experienced intense and constant pain. On a 0 to 10 point pain scale (10 is the worst pain possible), the pain level increased to a 10 within 5-6 minutes, was constant and seemed to originate from both molars and the gum and cheek for several inches surrounding the molars. After 10 minutes, the pain remained a 10 and it subsided after about 60 minutes to a 0.

To compare the relative ability of 6% elemental strontium only or 4% strontium+ Gallic Acid+ NAC, the subject ingested another dill pickle and the pain returned in a manner and quality identical to the description above.

The 6% strontium spray was applied by teaspoon and used to saturate both molars with a vigorous swishing action to force the liquid between and around the crowns. The liquid was then held in place by the tongue. After about 60 seconds, a second application by teaspoon was applied and only held with the tongue for 60 seconds.

The pain level that was at a 10 did not change for 2-3 minutes, then over 4-5 minutes was reduced to a 6-7, a noticeable and patient-appreciated pain reduction, yet too intense to tolerate over a long period of time. As for the first challenge. During minutes 10-12, the pain returned to 10.

After rinsing the mouth with water, the subject then applied 4% strontium+ Gallic Acid+ NAC in the manner described for strontium alone. For the first 4-5 minutes, there was no change in the pain. Starting about minutes 5-6, the pain started to diminish and by 7-8, it was reduced by 3-4 points to a 6-7. Within the next 3-4 minutes, the pain diminished to a 0-it was completely gone. The pain remained at 0 level.

During the next consecutive 4 nights, the subject re-experienced recurrences of pain in the two molars, apparently triggered by a range of spicy foods or due to unidentified foods. In each case, the pain commenced within minutes of eating dinner, typically precooked foods. The pain had a uniform profile, quality and time course and reached the same intense, intolerable 10 level of pain.

Each night the subject waited about 5 minutes, then treated the site with the 6% strontium-only formulation, followed with the 4% strontium+ Gallic Acid+ NAC. The response to the 6% strontium was remarkably consistent. The pain reduction always occurred within the first 6-8 minutes and was reduced to a maximum of 6-7. By 10 minutes after treatment, the pain always returned to a 10-level.

One night, the 6% strontium-only treatment was repeated without rinsing after the pain returned to 10 (2-3 minutes after the first treatment) and no cumulative or enhanced anti-pain benefit was observed. With this two-time strontium treatment, the pain was never reduced below a level 7 or 8, a noticeable but intolerable level.

After rinsing the mouth with water, the strontium+ Gallic Acid+ NAC treatment similarly demonstrated a highly consistent pattern of response. Within 10 to 12 minutes after treatment, the pain was completely gone (a 0 level) and remained gone for the remainder of each night.

No side effects including numbness, change of taste, tactile sensation or tongue motor strength was observed.

Several weeks later, both of the broken molars were extracted in the 59 year old male in preparation for later implants. Hydrocodone oral pain medications were prescribed and used up to the maximum recommended dose and frequency. Acetaminophen was also used in conjunction with the hyodrocodone.

One day after the extractions, the subject consumed soup that triggered intense 10-level pain within 1-2 minutes. The pain remained constant and level 10 and extended throughout the lower left jaw area.

The subject rinsed the mouth and used a dentist supplied washing agent to bathe the surgical sites without effect on the pain.

The subject then applied the 6% strontium-only formulation and at minutes 6-7, experienced a 1-2 point pain reduction—noticeable, but clinically ineffective.

The strontium+ Gallic Acid+ NAC was then applied in as in the previous manner and held in the surgical area with the tongue. During the first 4-5 minutes there was no pain reduction or increase of pain. At about minute 5, the pain started to diminish and by minutes 8-9 reached a 5 level of pain, a substantial reduction. No further pain reduction was observed in the next 2-3 minutes, and the strontium+ Gallic Acid+ NAC was reapplied. After about 4-5 minutes, the pain continued its reduction and after about 7-8 additional minutes, reached 0-level—complete pain cessation. The pain remained completely gone for the rest of the night in into the next day.

During the next week, the 59 year old subject was unable to avoid eating foods that did not trigger the pain, probably because the extraction sites were still slightly bleeding/oozing and were thus directly accessible to chemical irritants in foods.

Each night the pain recurred with minutes after consuming either solid food or liquids and reached the same unbearable intensity. Each night the treatment protocol listed above was repeated: 6% strontium—only formulation treatment first; mouth rinse; and 4% strontium+ Gallic Acid+ NAC treatment afterwards. For the next 5 nights, the pain recurred, reached the same intense level (10 using our scale), and at best, the 6% strontium only treatment reduced the pain by at most 3 points for 2-3 minutes, after which it returned to the previous 10 level.

The treatment with strontium+ Gallic Acid+ NAC was similarly reproducible. After the strontium only treatment and rinse, the strontium+ Gallic Acid+ NAC required 1-2 treatments during a 12-15 minute time after which the pain was always completely eliminated and remained absent for the remainder of the night and the next day. Within a week after the extractions, the extraction sites healed sufficiently to become non-sensitive to food derived pain inducers.

Example 2—Neuropathic Pain due to Nerve Compression

An 85 year old woman with severe macular degeneration, but otherwise in good health had experienced mild, bilaterally symmetric burning pain in both of her feet, slightly more intense on the bottom of her toes, but very evident and bothersome on the tops of both toes. The burning pain had been continuous, all day and all night and during the last 3 years and was made worse with walking. Typically at the end of a day the burning pain was at its worst. By all accounts it was relatively mild in that it did not bother her or interfere with walking or other activities during the day, but after a year or so after it started, she had to take her shoes off at night due to excessive burning.

In the last year, the intensity of the burning slowly increased to the point where her pain at night increased sufficiently so that she was unable to wear shoes with straps that wrapped around her toes—only fully unclosed shoes that did not contact her toes were tolerable, along with socks that provided cushioning. During the last 6 months, the intensity of the burning pain slowly increased so that she was unable to walk at night after dinner due to the burning pain. The pain during the day was not greatly increased nor was it excessively bothersome. The pain started to keep her from sleeping at night due to its constancy leading to her reduced daily walking.

The pain was, as it had always been, constantly present, essentially equal in intensity and distribution in both feet and worse at night and was not accompanied by any visible skin changes, redness or rash. The skin with the burning sensation also had numbness that extended over much of her feet in a bilaterally symmetrically manner.

She had no risk factor to explain the numbness or burning pain other then mild, chronic back pain with maximum pain emanating from the L-4, L-5, S-1 spinal roots. Since these nerves also innervate the top and bottom of feet, including the toes, the subject's physician suspects that the reported symptoms are due to compression of the spinal nerves at the L-4 to S-1 level and that the cause of the burning pain is chronic nerve compression that produced nerve damage, especially to Type C Nociceptors that transmit burning sensations. The resultant condition is a nerve compression neuropathic pain state.

The subject tested two formulations in a double-blind controlled manner. The product applications and data recording were performed by a retired aeronautical engineer.

At 8 PM both toes and the tops of both feet had the typical continuous burning pain sufficiently severe that shoes having any contact with the tops of her feet or toes were not worn. The pain levels were very similar.

Using a 0-10 point visual-analog scale, the subject was instructed to rank the foot with the most severe burning as a 10 and to assign the contralateral foot a score to reflect its pain level relative to the 10 level foot.

Her assignment was: Burning Pain Intensity in Left Foot—10; in Right Foot-8.

The Right Foot was then treated with a coded product labeled 'A' (the 4% strontium hydro gel) and the skin of the toes and the entire top of the foot was covered with the test material. No immediate effect was observed. Over the next 15-20 minutes, the burning pain continuously reduced from an 8 to a 5-6 level of pain. At 30 minutes treatment, the pain returned.

The Left Foot was then treated with a 2% strontium+ Gallic Acid+ NAC gel formulation in a manner identical to the Left Foot. Upon treatment, the pain remained a 10.

Within 1 minute after application, the pain reduced from a 10 to a 5 and by 5 minutes in was gone, a score of 0 and remained 0.

The next day at 8 PM, the Left foot had a 0 score and the subject reported that the pain was gone throughout the night . . . the first night in over three years that was pain free.

The right foot that had been treated with the 4% strontium gel had a burning pain score of 8 and had the score throughout the night, the subjects usual experience.

The Right foot was then treated with 2% strontium+ Gallic Acid+ NAC as previously described and within 5 minutes the pain was gone—a score of 0.

The numbness was not affected in either foot.

During the next 6 months, both feet have remained entirely pain free and the subject has been wearing shoes with toe wrap around bands and other shoes that directly contact the upper part of the feet and the toes with comfort. There has not been one recurrence of pain in either foot and the patient has resumed a normal ability to walk and wear the shoes of her choice. The numbness in both feet is unchanged and is the same as before the treatments occurred.

Example 3—Bracioradial Pruritis

A 40 year old male suffered from brachioradial pruritus for over 20 years, a neuropathic condition that is believed to be caused by compression of cervical nerves that innervate the mid-back and arms. He experienced moderate to severe itching typically most intense on his arms, neck and shoulders. Treatment with topical anti-itch drugs including 1% hydrocortisone, menthol-containing courter-irritants provided no anti-itch benefit. Topical diphenhydramine provided limited benefit only when the itching was mild.

During the last several years, the subject treated his condition with either strontium alone (4% or 6% elemental strontium) and with a spray formulation of strontium+ Gallic Acid+ NAC. A single treatment of severe itch with 6% elemental strontium alone provided limited anti-itch benefits. Reapplication 3 or 4 times over a 10-20 minute period increased that anti-itch benefit and reduced the itching by about 50%. When the 4% strontium+ Gallic Acid+ NAC was applied to severely itching skin, the severity of itching was typically reduced by 80% to 90% within about a minute after a single spray, and sometimes, the itching was completely eliminated. If itching remained, a second spray eliminated the remaining itching.

Subsequent blinded tests were performed in which either 4% strontium only or 6% strontium only was directly compared to 4% strontium+ Gallic Acid+ NAC. Since the subject's brachioradial pruritus typically produced itching of approximately equal intensity on both arms in a bilaterally-symmetrical pattern, strontium alone was applied to one arm and strontium+ Gallic Acid+ NAC was applied to the contralateral arm in a double-blinded manner and itch severity was reported by the subject. Repeated studies of this type demonstrated that the strontium+ Gallic Acid+ NAC was always substantially more effective then strontium alone and typically suppressed itching by 80% to 100% within several minutes. In contrast, strontium alone provided only limited relief with moderate to severe itch. The strontium+ Gallic Acid+ NAC also produced a substantial anti-itch benefit of much longer duration and frequently suppressed itching for more than a 24 hour period. Strontium alone provided only limited anti-itch benefit that typically lasted only several hours, at most.

Example 4—Bum Pain

A female was scalded by hot tea over the whole of her left hand and on her forearm up to about 4 inches above her wrist. A spray of strontium+ Caffeic Acid+ NAC was applied between half a minute and a minute after the incident. The intense pain started to recede shortly after application (probably about 30 seconds) and the redness of the hand and arm quickly became less angry. Within about 5 minutes, the subject no longer felt any discomfort and the redness had disappeared. There was no need for any further application of the spray and the redness did not return and she suffered no blistering or bubbling. Her left hand was tender for a while in the sense that she used the other hand to carry things for the rest of the evening. The incident occurred at about 7.30 in the evening. The following day when she woke up, her hand was completely normal.

Example 5—Wasp Sting

An adult male subject observed a wasp sting on the back of his right hand. Within about 30 seconds, the subject experienced increased burning pain and accompanying mild itching that rapidly increased in severity. Swelling and redness rapidly developed over the next 2-3 minutes and the pain intensified to an unbearable level. The subject then applied the same spray from Example 3. Within the first several minutes the pain was unaffected. During the next 5 minutes, the pain was reduced and after approximately 6-7 minutes the pain was completely gone. There was no visible reduction in the redness or the swelling that produced a swollen circular area of skin about 2-3 inches in diameter with a height of about ¼ of an inch. The pain and itching did not return and over the next hour or so, the swelling and redness diminished and disappeared.

Example 6—Chronic Pruritis

A 72 year old adult male subject suffered from a chronic pruritic dry patch of skin on his right ankle that had been itching more or less constantly for several months. Periodic treatment with a 4% elemental strontium-containing hydro-gel or a 6% elemental strontium-containing aqueous spray formulation provided moderate itch relief that typically lasted several hours, after which the itching returned. Treatment with the spray described in Example 3 completely reduced the itching within several minutes that lasted for over a day. Subsequent re-treatment with the same spray produced similar and complete itch relief that lasted from about 12 hours to over 24 hours.

Example 7—Synthesis of Thioester Bonded Gallic Acid and NAC

Synthesis 1: The gallic acid carboxyl group was attached to the NAC sulfhydryl group to create a thioester bond. Gallic acid was reacted with acetic anhydride and sulfuric acid to protect the three hydroxyl groups on the benzene ring. The resulting compound, 3,4,5-triacetoxybenzoic acid (compound A), was precipitated in water, filtered and dried under vacuum.

Synthesis 2: Compound A was reacted with oxalyl chloride and dichloromethane to substitute chlorine for the remaining hydroxyl group. The resulting compound, which was the corresponding acid chloride, (compound B) was purified using toluene and dried under vacuum.

Synthesis 3: Compound B was reacted with 1H-benzo[d] [1,2,3] triazole in acetonitrile. The resulting compound, 5-(1H-benzo[d] [1,2,3]triazole-1-1 carbonyl)benzene-1,2,3-triyl triacetate (compound C), was filtered with cold water and dried under vacuum.

Synthesis 4: Compound C in 1,4 dioaxane was reacted with N-acetyl cysteine, potassium acetate, and water. The resulting compound (compound D), was acidified with hydrochloride, washed with ethyl acetate, and evaporated.

Synthesis 5: Compound D was reacted with water and ammonium hydroxide to hydrolyze the acetyl protective groups added in the first synthesis. The resulting compound is the thioester bound gallic acid and NAC (GA:NAC)

The GA:NAC was reacted with strontium nitrate. The final compound, strontium tripartite with thioester bond (Sr:GA:NAC), was precipitated out using acetone and vacuum dried.

Example 8—Octanol-Water Partition Co-Efficient, Determination of cLogP

The strontium tripartite with thioester bond compound was partitioned between octanol and water in order to determine the water solubility properties of the compound. The partition co-efficient, cLogP, was determined by using high performance liquid chromatography (HPLC). The cLogP for Sr:GA:NAC was −0.209, which means that the final compound has similar solubility to ethanol.

Example 9—Cleaving of Thioester Bond Using Human Enzymes

The strontium tripartite with thioester bond compound was subjected to enzymatic cleavage with three different enzymes, human carboxylesterase I (CES1), human carboxylesterase II (CES2), and S9 liver microsomes enzyme For each of the three enzymes evaluated, Sr:GA:NAC was added to four sample tubes, A, B, C, and D. Enzyme was added to tubes A and B and gallic acid was added to tube D. The samples were tested by monitoring the UV counts at time points 5, 60, 180, 360, 540, 1380 minutes by HPLC using a C18 column.

The results demonstrated that all three enzymes cleaved the thioester bond to release NAC and gallic acid.

The embodiments discussed above are provided to give those of ordinary kill in the art a complete disclosure and description of how to make and use the embodiments of the methods, and are not intended to limit the scope of what the inventor regards as his invention. Modifications of the above-described modes (for carrying out the invention that are obvious to persons of skill in the art) are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of treating pruritis in a subject, the method comprising topically administering to the subject a composition comprising a complex of:
   a divalent cationic strontium moiety;
   a cysteine-based anti-oxidant moiety selected from the group consisting of cysteine, N-acetyl cysteine, N-acetyl cysteinate, N,S-diacetylcysteine, and esters thereof; and
   a polyhydroxyphenol moiety selected from the group consisting of gallic acid, caffeic acid, quercetin, luteolin, epigallocatechin gallate, epigallocatechin, epicatechin gallate, genistein, myricetin, and esters thereof;
   in a suitable carrier vehicle,
   wherein the cysteine-based anti-oxidant moiety and the polyhydroxyphenol moiety are conjugated together by a cleavable bond.

2. The method of claim 1, wherein the divalent cationic strontium moiety is a strontium salt selected from the group consisting of strontium chloride, strontium chloride hexahydrate, strontium sulfate, strontium carbonate, strontium nitrate, strontium hydroxide, strontium hydrosulfide, strontium oxide, strontium acetate, strontium glutamate, strontium aspartate, strontium malonate, strontium maleate, strontium citrate, strontium threonate, strontium lactate, strontium pyruvate, strontium ascorbate, strontium alpha-ketoglutarate, and strontium succinate.

3. The method of claim 1, wherein the cysteine-based anti-oxidant moiety is N-acetyl cysteine or esters thereof.

4. The method of claim 1, wherein the polyhydroxyphenol moiety is gallic acid or esters thereof.

5. The method of claim 1, wherein the cysteine-based anti-oxidant moiety is N-acetyl cysteine or esters thereof and the polyhydroxyphenol moiety is gallic acid or esters thereof.

6. The method of claim 1, wherein the cleavable bond is selected from the group consisting of a peptide bond, an ester bond, a thioester bond, an enzymatically cleavable bond, a disulfide bond, and a pH dependent bond.

7. The method of claim 6, wherein the cleavable bond is a thioester bond.

8. The method of claim 1, wherein the composition further comprises a polymer.

9. The method of claim 8, wherein the polymer is selected from the group consisting of polyvinylpyrrolidone, cyclodextrins, carrageenan, alginic acid, xanthan gum, sulfated polysaccharides, pentosane polysulfate, chondroitin sulfate, dextran sulfate, and heparin sulfate.

10. A method of treating pruritis in a subject, the method comprising topically administering to the subject a composition comprising a complex of:
   a divalent cationic strontium moiety;
   a cysteine-based anti-oxidant moiety; and
   a polyhydroxyphenol moiety;

wherein the cysteine-based anti-oxidant moiety and the polyhydroxyphenol moiety are conjugated together by a thioester bond.

11. The method of claim 10, wherein the divalent cationic strontium moiety is a strontium salt selected from the group consisting of strontium chloride, strontium chloride hexahydrate, strontium sulfate, strontium carbonate, strontium nitrate, strontium hydroxide, strontium hydrosulfide, strontium oxide, strontium acetate, strontium glutamate, strontium aspartate, strontium malonate, strontium maleate, strontium citrate, strontium threonate, strontium lactate, strontium pyruvate, strontium ascorbate, strontium alpha-ketoglutarate, and strontium succinate.

12. The method of claim 10, wherein the cysteine-based anti-oxidant moiety is N-acetyl cysteine or esters thereof.

13. The method of claim 10, wherein the polyhydroxyphenol moiety is gallic acid or esters thereof.

14. The method of claim 10, wherein the cysteine-based anti-oxidant moiety is N-acetyl cysteine or esters thereof and the polyhydroxyphenol moiety is gallic acid or esters thereof.

15. The method of claim 10, wherein the composition further comprises a polymer.

16. The method of claim 15, wherein the polymer is selected from the group consisting of polyvinylpyrrolidone, cyclodextrins, carrageenan, alginic acid, xanthan gum, sulfated polysaccharides, pentosane polysulfate, chondroitin sulfate, dextran sulfate, and heparin sulfate.

17. A method of treating pruritis in a subject, the method comprising topically administering to the subject a composition comprising a complex of:

a strontium nitrate moiety;

an N-acetyl cysteine moiety; and a gallic acid moiety;

wherein the N-acetyl cysteine moiety and the gallic acid moiety are conjugated together by a thioester bond.

18. The method of claim 17, wherein the composition further comprises a polymer.

19. The method of claim 18, wherein the polymer is selected from the group consisting of polyvinylpyrrolidone, cyclodextrins, carrageenan, alginic acid, xanthan gum, sulfated polysaccharides, pentosane polysulfate, chondroitin sulfate, dextran sulfate, and heparin sulfate.

* * * * *